(12) United States Patent
Dong et al.

(10) Patent No.: US 11,981,718 B2
(45) Date of Patent: May 14, 2024

(54) DUAL-FUNCTION PROTEIN FOR LIPID AND BLOOD GLUCOSE REGULATION

(71) Applicant: AMPSOURCE BIOPHARMA SHANGHAI INC., Shanghai (CN)

(72) Inventors: Zhao Dong, Shanghai (CN); Chi Zhou, Shanghai (CN); Xiong Feng, Shanghai (CN); Jiyu Zhang, Shanghai (CN); Shixiang Jia, Shanghai (CN); Qiang Li, Shanghai (CN)

(73) Assignee: AMPSOURCE BIOPHARMA SHANGHAI INC., Shanghai (CN)

( * ) Notice: Subject to any disclaimer, the term of this patent is extended or adjusted under 35 U.S.C. 154(b) by 0 days.

(21) Appl. No.: 16/884,905

(22) Filed: May 27, 2020

(65) Prior Publication Data

US 2021/0371488 A1 Dec. 2, 2021

(51) Int. Cl.
| | | |
|---|---|---|
| *A61K 38/26* | (2006.01) | |
| *A61K 38/18* | (2006.01) | |
| *C07K 14/50* | (2006.01) | |
| *C07K 14/605* | (2006.01) | |
| *C12N 15/85* | (2006.01) | |
| *A61K 38/00* | (2006.01) | |

(52) U.S. Cl.
CPC ............ *C07K 14/605* (2013.01); *C07K 14/50* (2013.01); *C12N 15/85* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,818,679 A | 4/1989 | Chasin et al. | |
| 6,103,501 A | 8/2000 | Boime et al. | |
| 6,225,449 B1 | 5/2001 | Boime | |
| 6,531,121 B2 * | 3/2003 | Brines ................ | A61K 38/1816 514/912 |
| 7,189,827 B2 | 3/2007 | Feige et al. | |
| 8,163,889 B2 | 4/2012 | Kim et al. | |
| 8,304,224 B2 | 11/2012 | Lovgren | |
| 9,023,791 B2 | 5/2015 | Boettcher et al. | |
| 9,266,935 B2 | 2/2016 | Boettcher et al. | |
| 10,010,622 B2 | 7/2018 | Dumont et al. | |
| 10,287,564 B2 | 5/2019 | Hong et al. | |
| 2001/0012628 A1 | 8/2001 | Agarwal et al. | |
| 2003/0211580 A1 | 11/2003 | Lustbader | |
| 2005/0250185 A1 | 11/2005 | Murphy et al. | |
| 2006/0263849 A1 * | 11/2006 | Glaesner ................ | A61P 43/00 435/325 |
| 2007/0129298 A1 | 6/2007 | Krebber et al. | |
| 2009/0042784 A1 | 2/2009 | Krarup | |
| 2010/0081614 A1 | 4/2010 | Fares et al. | |
| 2013/0129724 A1 * | 5/2013 | Boettcher ................ | A61P 3/04 424/134.1 |
| 2015/0203558 A1 | 7/2015 | Fares et al. | |
| 2015/0353911 A1 | 12/2015 | Salas et al. | |
| 2016/0115467 A1 | 4/2016 | Salas | |
| 2017/0029505 A1 * | 2/2017 | Griffin ................ | A61P 1/18 |
| 2018/0110834 A1 * | 4/2018 | Depaoli ............ | G01N 33/6848 |
| 2018/0236037 A1 * | 8/2018 | Göbel ................ | A61K 47/60 |
| 2018/0360932 A1 * | 12/2018 | Fima ................ | C12N 9/644 |
| 2019/0184026 A1 | 6/2019 | Li et al. | |
| 2019/0365867 A1 | 12/2019 | Li et al. | |
| 2020/0157185 A1 | 5/2020 | Gao et al. | |
| 2022/0089669 A1 * | 3/2022 | Mullican ................ | C12N 15/62 |

FOREIGN PATENT DOCUMENTS

| | | |
|---|---|---|
| CA | 3059662 A1 | 2/2018 |
| CN | 1290301 A | 4/2001 |
| CN | 1889937 A | 1/2007 |
| CN | 101010338 A | 8/2007 |
| CN | 1802386 B | 12/2010 |
| CN | 102625811 A | 8/2012 |
| CN | 102802657 A | 11/2012 |
| CN | 103328502 A | 9/2013 |
| CN | 103539860 A | 1/2014 |

(Continued)

OTHER PUBLICATIONS

Justice et al. Using the mouse to model human disease: increasing validity and reproducibility, Disease, Models & Mechanisms 9: 101-103, (2016) (Year: 2016).*
Ferreira et al. Comparison of drug efficacy in two animal models of type 2 diabetes: A systemic review and meta-analysis. European Journal of Pharmacology 879:173153 (2020) (Year: 2020).*
U.S. Appl. No. 16/604,088, filed Oct. 9, 2019, Ampsource.
Tang Y et al, "Selection of Linkers for a Catalytic Single-chain Antibody Using Phage Display Technology", J Biol Chem, 1996, 271(26):15682-15686.
Arai R et al, "Design of the linkers which effectively separate domains of a bifunctional fusion protein", Protein Engineering, 2001, 14(8):529-532.

(Continued)

*Primary Examiner* — Elizabeth C. Kemmerer
*Assistant Examiner* — Regina M DeBerry
(74) *Attorney, Agent, or Firm* — FINNEGAN, HENDERSON, FARABOW, GARRETT & DUNNER LLP

(57) ABSTRACT

The present disclosure relates to a dual-function protein for regulating blood glucose and lipid metabolism, wherein said dual-function protein comprises a human GLP-1 analog and human FGF21. In the present disclosure, provided is a method for preparing said dual function protein, and also provided is the use of said dual-function protein in the preparation of a biological substance for treating type 2 diabetes, obesity, dyslipidemia, fatty liver disease and/or metabolic syndrome. The dual-function protein provided in the present disclosure can synergistically regulate blood glucose and lipid levels in vivo, and satisfy multiple requirements for patients with type 2 diabetes such as lowering blood glucose, relieving hepatic steatosis, reducing body weight and improving metabolic disorders of circulating lipids.

8 Claims, 13 Drawing Sheets

Specification includes a Sequence Listing.

(56) References Cited

FOREIGN PATENT DOCUMENTS

| | | |
|---|---|---|
| CN | 103539861 A | 1/2014 |
| CN | 103539868 A | 1/2014 |
| CN | 103539869 A | 1/2014 |
| CN | 103649127 A | 3/2014 |
| CN | 103827142 A | 5/2014 |
| CN | 103945871 A | 7/2014 |
| CN | 104024273 B | 9/2014 |
| CN | 104039831 A | 9/2014 |
| CN | 104114183 A | 10/2014 |
| CN | 104427994 A | 3/2015 |
| CN | 104519897 A | 4/2015 |
| CN | 104519912 A | 4/2015 |
| CN | 104693270 A | 6/2015 |
| CN | 104903352 A | 9/2015 |
| CN | 105153313 A | 12/2015 |
| CN | 104774269 | 2/2016 |
| CN | 103897064 B | 5/2016 |
| CN | 105753945 B | 7/2016 |
| CN | 106256835 A | 12/2016 |
| CN | 106279436 A | 1/2017 |
| CN | 106279437 A | 1/2017 |
| CN | 106317226 B | 9/2017 |
| CN | 107474138 | 12/2017 |
| CN | 110028587 A | 7/2019 |
| EA | 005404 B1 | 2/2005 |
| EA | 201291480 | 9/2013 |
| EP | 1624891 B1 | 8/2009 |
| JP | 2014-522838 | 9/2014 |
| KR | 2010-0099179 | 9/2010 |
| KR | 101027427 B1 | 4/2011 |
| RU | 2312868 C2 | 12/2007 |
| WO | WO 2006/053301 | 5/2000 |
| WO | WO 03/011213 | 2/2003 |
| WO | WO2003/061712 | 7/2003 |
| WO | WO 2004/110472 | 12/2004 |
| WO | WO 2005/000892 | 1/2005 |
| WO | WO2005058953 A | 6/2005 |
| WO | WO 2005/091944 | 10/2005 |
| WO | WO 2005/113606 | 12/2005 |
| WO | WO2006/028595 | 3/2006 |
| WO | WO2006/028714 | 3/2006 |
| WO | WO 2006/050247 | 5/2006 |
| WO | WO2006/065582 | 6/2006 |
| WO | WO2007090584 | 8/2007 |
| WO | WO 2008/121563 | 10/2008 |
| WO | WO 2009/149171 | 12/2009 |
| WO | WO 2010/042747 | 4/2010 |
| WO | WO 2010/084169 | 7/2010 |
| WO | WO 2010/129503 | 11/2010 |
| WO | WO 2010/129600 | 11/2010 |
| WO | WO 2010/142665 | 12/2010 |
| WO | WO 2011/071783 | 6/2011 |
| WO | WO2011092234 | 8/2011 |
| WO | WO 2011/130417 | 10/2011 |
| WO | WO 2012/010553 | 1/2012 |
| WO | WO 2012/066075 | 5/2012 |
| WO | WO 2012/158704 | 11/2012 |
| WO | WO 2012/170438 | 12/2012 |
| WO | WO 2012/175751 | 12/2012 |
| WO | WO 2013/049234 | 4/2013 |
| WO | WO 2013/049247 | 4/2013 |
| WO | WO2013049247 | 4/2013 |
| WO | WO2013096386 A | 6/2013 |
| WO | WO 2013/100702 | 7/2013 |
| WO | WO2013121416 | 8/2013 |
| WO | WO2013152351 A2 | 10/2013 |
| WO | WO 2013/188181 | 12/2013 |
| WO | WO2013185114 | 12/2013 |
| WO | WO2014026954 A1 | 2/2014 |
| WO | WO2014037373 | 3/2014 |
| WO | WO2014/052490 | 4/2014 |
| WO | WO2014106015 A | 7/2014 |
| WO | WO 2016/114633 | 7/2016 |
| WO | WO 2017/074123 | 5/2017 |
| WO | 2018/032786 A1 | 2/2018 |
| WO | WO-2018032637 A1 * | 2/2018 ............ A61K 38/37 |
| WO | 2018/166461 A1 | 9/2018 |
| WO | 2019/243557 A1 | 12/2019 |

OTHER PUBLICATIONS

Luo D et al., "Flexibility between the Protease and Helicase Domains of the Dengue Virus NS3 Protein Conferred by the Linker Region and Its Functional Implications", J Biol Chem., 2010, 285(24):18817-18827.

Uchida H et al, "Analysis of binding properties between 20 kDa human growth hormone (hGH) and hGH receptor (hGHR): the binding affinity for hGHR extracellular domain and mode of receptor dimerization", J Mol Endocrinol., 1999, 23: 347-353.

Gilbert G E et al, "Specific Membrane Binding of Factor VIII Is Mediated by O-Phospho-L-serine, a Moiety of Phosphatidylserine", Biochemistry, 1993, 32(37): 9577-9585.

Salas J et al. "Enhanced Pharmacokinetics of Factor VIIa as a Monomeric Fc Fusion", Thrombosis research, 2015, 135(5):970-976.

Dickneite G, "Prothrombin complex concentrate versus recombinant factor VIIa for reversal of coumarin anticoagulation", Thrombosis Research (2007) 119, 643-651, Germany.

International Search Report for International Application No. PCT/CN2016/106011, dated Feb. 28, 2017.

Li G et al, "Construction of a Linker Library with Widely Controllable Flexibility for Fusion Protein Design", Appl. Microbiol Biotechnol., 2016, 100:215-225.

Joshua S Klein et al, "Design and Characterization of Structured Protein Linkers with Differing Flexibilities", Protein Engineering, 2014, 27(10):325-330.

International Search Report for International Application No. PCT/CN2016/106010, dated Mar. 15, 2017.

Skosyrev, V S et al. "The Dependence of Stability of the Green Fluorescent Protein-Obelin Hybrids on the Nature of Their Constituent Modules and the Structure of the Amino Acid Linker", Russian Journal of Bioorganic Chemistry 27, 323-329 (2001).

Treetharnmathurot B et al, "Effect of PEG molecular weight and linking chemistry on the biological activity and thermal stability of PEGylated trypsin", Int J Pharma, 2008, 357:252-259.

Wen D et al, "Discovery and Investigation of O-Xylosylation in Engineered Proteins Containing a (GGGGS)n Linker", Anal. Chem., 2013, 85:4805-4812.

International Search Report for International Application No. PCT/CN2017/079871, dated Jul. 7, 2017.

Turecek P.L. et al., "BAX 855, a PEGylated rFVIII product with prolonged half-life", Hamostaseologie 2012, 32:S29-S38.

Coskun T et al, "Fibroblast growth factor 21 corrects obesity in mice", Endocrinology, 2008, 149(12):6018-6027.

Berglund Ed et al, "Fibroblast growth factor 21 controls glycemia via regulation of hepatic glucose flux and insulin sensitivity", Endocrinology, 2009, 150(9):4084-4093.

Xu J et al, "Acute glucose-lowering and insulin-sensitizing action of FGF21 in insulin-resistant mouse models-association with liver and adipose tissue effect", Am J Physiol Endocrinol Metab, 2009, 297(5):E1105-1114.

Kharitonenkov A et al, "The metabolic state of diabetic monkeys is regulated by fibroblast growth factor-21", Endocrinology, 2007, 148(2):774-781.

Hecht R et al, "Rationale-based engineering of a potent long-acting FGF21 analog for the treatment of type 2 diabetes", PLoS One, 2012, 7:e49345.

Collins PW et al., "Recombinant long-acting glycoPEGylated factor IX in hemophilia B: a multinational randomized phase 3 trial", Blood, 2014, 124(26):3880-3886.

Hart G et al., "FVIIa-CTP and FIX-CTP are novel long-acting coagulation factors with prolonged hemostatic activity in hemophilic animal models: PO-TU-025", Haemophilia, 2012, 18.

Peters RT et al, "Prolonged activity of factor IX as a monomeric Fc fusion protein", Blood, 2010, 115(10):2057-2064.

(56) References Cited

OTHER PUBLICATIONS

Broze et al, "Purification and properties of human coagulation factor VII", J Biol Chem, 1980, 255: 1242-1247.
Golor G et al, "Safety and pharmacokinetics of a recombinant fusion protein linking coagulation factor VIIa with albumin in healthy volunteers", J Thromb Haemost, 2013, 11:1977-85.
Weimer T et al., "Prolonged in-vivo half-life of factor VIIa by fusion to albumin", Thromb Haemost, 2008, 99: 659-667.
Ljung R et al, "40K glycoPEGylated, recombinant FVIIa: 3-month, doubleblind, randomized trial of safety, pharmacokinetics and preliminary efficacy in hemophilia patients with inhibitors", J Thromb Haemost, 2013, 11(7):1260-1268.
Hagen FS et al, "Characterization of a cDNA coding for human factor VII", Proc Natl Acad Sci USA, 1986, 83(8):2412-2416.
Hedner U et al, "Use of human factor VIIa in the treatment of two hemophilia A patients with high-titer inhibitors", J Clin Invest, 1983, 71:1836-1841.
Kisiel et al, "Enzymological aspects of blood coagulation", Behring Inst Mitt, 1983, 73:29-42.
Pedersen AH et al, "Autoactivation of human recombinant coagulation factor VII", Biochemistry, 1989, 28:9331-9336.
Bjoern S et al, "Activation of coagulation factor VII to VIIa", Res Disclosure, 1986, 269:564-565.
Li J F et al, "Design of Linker Peptides and Its Application in Fusion Protein", J Food Sci Biotech, 2015, 34:1121-1127.
Calo et al, "Enhancing the longevity and in vivo potency of therapeutic proteins: The power of CTP", Precision Medicine, 2015, 2:e989.
International Search Report for International Application No. PCT/CN2016/106012, dated May 22, 2017.
International Search Report for International Application No. PCT/CN2017/079872, dated Jul. 5, 2017.
Beenken A. et al. "The FGF family: biology, pathophysiology and therapy" Nature Reviews Drug Discovery Mar. 2009 vol. 8, pp. 235-253.
Datta-Manna A. et al. "Influence of improved FcRn binding on the subcutaneous bioavailability of monoclonal antibodies in cynomolgus monkeys" mAbs, 4:2, 2012, pp. 267-273.
Dong J. Q. et al. "Pharmacokinetics and pharmacodynamics of PF-05231023, a novel long-acting FGF21 mimetic, in a first-in-human study" Br J Clin Pharmacol, 2015, 80:5, pp. 1051-1063.
Dutchak P. A. et al. "Fibroblast Growth Factor-21 Regulates PPARg Activity and the Antidiabetic Actions of Thiazolidinediones" Cell 148, Feb. 3, 2012, pp. 556-567.
Fares F. A. et al. "Design of a long-acting follitropin agonist by fusing the C-terminal sequence of the chorionic gonadotropin B subunit to the follitropin B subunit" Proc. Natl. Acad. Sci. USA, vol. 89, pp. 4304-4308, May 1992, pp. 4304-4308.
Gaich G. et al. "The Effects of LY2405319, an FGF21 Analog, in Obese Human Subjects with Type 2 Diabetes" Cell Metabolism 18, Sep. 3, 2013, pp. 333-340.
Hinton P. R. et al. "Engineered Human IgG Antibodies with Longer Serum Half-lives in Primates" J. Biol. Chem. 2004, 279, pp. 6213-6216.
Hinton P. R. et al. "An Engineered Human IgG1 Antibody with Longer Serum Half-Life" J Immunol 2006; 176, pp. 346-356.
Jefferis R. et al. "IgG-Fc-mediated effector functions: molecular definition of interaction sites for effector ligands and the role of glycosylation" Immunological Reviews 1998 vol. 163, pp. 59-76.

Kharitonenkov A. et al. "FGF-21 as a novel metabolic regulator" The Journal of Clinical Investigation vol. 115 No. 6 Jun. 2005, pp. 1627-1635.
Knudsen L. B. "Glucagon-like Peptide-1: The Basis of a New Class of Treatment for Type 2 Diabetes" *J. Med. Chem.* 2004, 47, pp. 4128-4134.
Lin Z. et al. "Fibroblast Growth Factor 21 Prevents Atherosclerosis by Suppression of Hepatic Sterol Regulatory Element-Binding Protein-2 and Induction of Adiponectin in Mice" Circulation vol. 131, (21) 2015, (54 pages).
Micanovic R. et al. "Different Roles of N- and C-Termini in the Functional Activity of FGF21" J. Cell. Physiol. 219, 2009, pp. 227-234.
Moore D. D. "Sister Act" Science, vol. 316 Jun. 8, 2007, pp. 1436-1438.
Neidigh J. W. et al. "Exendin-4 and Glucagon-like-peptide-1: NMR Structural Comparisons in the Solution and Micelle-Associated States" *Biochemistry* 2001, 40, pp. 13188-13200.
Petit J.-M. et al. "GLP-1 receptor agonists in NAFLD" Diabetes & Metabolism 43 (2017) S28-S33.
Radaelli M. G. et al. "NAFLD/NASH in patients with type 2 diabetes and related treatment options" Journal of Endocrinological Investigation (2018) 41, pp. 509-521.
Roopenian D. C. et al. "FcRn: the neonatal Fc receptor comes of age" Nature Review Immunology vol. 7 Sep. 2007 pp. 715-725.
Shields R. L. et al. "High Resolution Mapping of the Binding Site on Human IgG1 for FcgRI, FcgRII, FcgRIII, and FcRn and Design of IgG1 Variants with Improved Binding to the FcgR" J. Biol. Chem. 2001, 276, pp. 6591-6604.
Wu X. et al. "Separating mitogenic and metabolic activities of fibroblast growth factor 19 (FGF19)" PNAS, Aug. 10, 2010, vol. 107, No. 32, pp. 14158-14163.
Xu J. et al. "Fibroblast Growth Factor 21 Reverses Hepatic Steatosis, Increases Energy Expenditure, and Improves Insulin Sensitivity in Diet-Induced Obese Mice" Diabetes, vol. 58, Jan. 2009, pp. 250-259.
Yie J. "FGF21 N- and C-termini play different roles in receptor interaction and activation" FEBS Letters 583 (2009) pp. 19-24.
Doron et al., Enhancing the longevity and in vivo potency of therapeutic proteins: The power of CTP, *Precision Medicine*, 2015, 2: e989.
Maeda Y, et al. Engineering of Functional Chimeric Protein G-Vargula Luciferase, *Anal Biochem.* 1997, 249(2):147-52.
Orlando M., Modification of proteins and low molecular weight substances with hydroxyethyl starch (HES), Inauguraldissertation, Giesen, 2003, p. 166, p. 15.
Chen X, Zaro J L, Shen W C. Fusion Protein Linkers: Property, Design and Functionality, *Adv Drug Deliv Rev*, 2013, 65(10): 1357-1369.
Supplementary European Search Report for EP17840761, dated Jan. 20, 2021.
Non-Final Office Action of U.S. Appl. No. 16/326,412, dated May 13, 2020.
Final Office Action of U.S. Appl. No. 16/326,412, dated Oct. 27, 2020.
Zhang et al., "Fibroblast growth factor 21, the endocrine FGF pathway and novel treatments for metabolic syndrome," Drug Discovery Today, 2014, 19(5):579-589.

\* cited by examiner

```
SEQ ID NO:33    1                   M   R   S   L   G   A   L   L   L   L   L   S   A   C   L   A
SEQ ID NO:34    1 actagtcgccaccATGAGGAGCCTCGGGGCCCTGCTCTTGCTGCTGAGCGCCTGCCTGGC
               17 V   S   A   H   G   E   G   T   F   T   S   D   V   S   S   Y   L   E   E   Q
               61 GGTGAGCGCTCATGGCGAAGGCACCTTCACCTCCGATGTGAGCAGCTACCTGGAAGAGCA
               37 A   A   K   E   F   I   A   W   L   V   K   G   G   G   G   G   G   G   S   G
              121 GGCCGCTAAAGAGTTTATCGCTTGGCTGGTGAAGGAGGAGGAGGCGGAGGCGGAAGCGG
               57 G   G   G   S   G   G   G   G   S   H   P   I   P   D   S   S   P   L   L   Q
              181 CGGCGGAGGCAGCGGCGGAGGCGGCAGCCACCCTATTCCCGATAGCTCCCCCCTCCTGCA
               77 F   G   G   Q   V   R   Q   R   Y   L   Y   T   D   D   A   Q   Q   T   E   A
              241 GTTCGGAGGCCAGGTGAGGCAGCGGTACCTGTACACCGACGACGCTCAGCAGACCGAAGC
               97 H   L   E   I   R   E   D   G   T   V   G   G   A   A   D   Q   S   P   E   S
              301 TCACCTGGAGATCAGGGAGGATGGAACCGTCGGCGGAGCTGCTGACCAGTCCCCCGAGAG
              117 L   L   Q   L   K   A   L   K   P   G   V   I   Q   I   L   G   V   K   T   S
              361 CCTGCTGCAGCTGAAGGCCCTGAAGCCCGGAGTCATCCAGATCCTGGGCGTGAAGACCTC
              137 R   F   L   C   Q   R   P   D   G   A   L   Y   G   S   L   H   F   D   P   E
              421 CCGGTTTCTGTGTCAGCGGCCCGATGGAGCCCTGTACGGCTCCCTGCATTTTGACCCCGA
              157 A   C   S   F   R   E   L   L   L   E   D   G   Y   N   V   Y   Q   S   E   A
              481 GGCCTGTAGCTTCAGGGAGCTGCTGCTGGAAGACGGCTACAACGTGTACCAGAGCGAAGC
              177 H   G   L   P   L   H   L   P   G   N   K   S   P   H   R   D   P   A   P   R
              541 TCACGGACTGCCCCTGCACCTGCCTGGCAACAAATCCCCTCACAGGGACCCCGCTCCCAG
              197 G   P   A   R   F   L   P   L   P   G   L   P   P   A   P   P   E   P   P   G
              601 GGGACCTGCCAGGTTCCTGCCTCTGCCCGGACTGCCTCCTGCTCCTCCCGAACCTCCTGG
              217 I   L   A   P   Q   P   P   D   V   G   S   S   D   P   L   S   M   V   G   P
              661 CATCCTCGCTCCTCAGCCCCCTGATGTCGGCAGCAGCGACCCTCTGTCCATGGTCGGCCC
              237 S   Q   G   R   S   P   S   Y   A   S   G   S   G   G   G   G   S   G   G   G
              721 CAGCCAAGGCAGGAGCCCTTCCTACGCTTCCGGATCCGGTGGCGGTGGCTCCGGTGGAGG
              257 G   S   G   G   G   G   S   G   G   G   G   S   G   G   G   G   S   S   S   S
              781 CGGAAGCGGCGGTGGAGGATCAGGCGGTGGAGGTAGCGGCGGAGGCGGTAGCTCCAGCTC
              277 S   K   A   P   P   P   S   L   P   S   P   S   R   L   P   G   P   S   D   T
              841 TAGTAAAGCTCCCCCTCCTTCCCTGCCCTCACCCTCAAGACTGCCTGGACCTTCCGACAC
              297 P   I   L   Q   V   E   C   P   P   C   P   A   P   P   V   A   G   P   S
              901 TCCCATCCTGCCACAGGTGGAGTGCCCTCCATGTCCAGCACCCCCTGTCGCAGGTCCATC
              317 V   F   L   F   P   P   K   P   K   D   Q   L   M   I   S   R   T   P   E   V
              961 TGTGTTCCTGTTTCCACCCAAGCCTAAAGACCAGCTGATGATCTCCCGCACCCCAGAAGT
              337 T   C   V   V   V   D   V   S   H   E   D   P   E   V   Q   F   N   W   Y   V
             1021 CACCTGTGTGGTCGTGGATGTGAGCCATGAAGACCCCGAGGTCCAGTTCAATTGGTACGT
              357 D   G   V   E   V   H   N   A   K   T   K   P   R   E   E   Q   F   N   S   T
             1081 GGATGGCGTCGAGGTGCACAACGCTAAGACAAAACCTAGAGAAGAGCAGTTCAACTCTAC
              377 F   R   V   V   S   V   L   T   V   V   H   Q   D   W   L   N   G   K   E   Y
             1141 CTTTCGCGTCGTGAGTGTGCTGACAGTCGTGCACCAGGACTGGCTGAATGGCAAGGAGTA
              397 K   C   K   V   S   N   K   G   L   P   A   S   I   E   K   T   I   S   K   T
             1201 TAAGTGCAAAGTGAGCAACAAAGGACTGCCTGCCTCAATCGAAAAGACTATTTCCAAGAC
              417 K   G   Q   P   R   E   P   Q   V   Y   T   L   P   P   S   R   E   E   M   T
             1261 CAAAGGACAGCCAAGAGAGCCCCAGGTGTACACCCTGCCTCCAAGCCGCGAAGAGATGAC
              437 K   N   Q   V   S   L   T   C   L   V   K   G   F   Y   P   S   D   I   A   V
             1321 TAAAAATCAGGTCTCTCTGACCTGTCTGGTGAAGGGGTTTTATCCTAGTGATATCGCCGT
              457 E   W   E   S   N   G   Q   P   E   N   N   Y   K   T   T   P   P   M   L   D
             1381 GGAATGGGAGTCAAACGGTCAGCCAGAGAACAATTACAAGACCACACCCCCTATGCTGGA
              477 S   D   G   S   F   F   L   Y   S   K   L   T   V   D   K   S   R   W   Q   Q
             1441 CAGCGATGGGTCTTTCTTTCTGTATAGCAAACTGACAGTGGACAAGTCTCGGTGGCAGCA
              497 G   N   V   F   S   C   S   V   L   H   E   A   L   H   N   H   Y   T   Q   K
             1501 GGGTAACGTCTTCTCTTGCAGTGTGCTGCACGAAGCACTGCACAATCATTACACCCAGAA
              517 S   L   S   L   S   P   G   K   *
             1561 GTCACTGTCACTGAGCCCAGGAAAATGAatccaacgggctgatgctgcaccaactgtatc
             1621 cgaattc
```

Fig. 1

DUAL-FUNCTION PROTEIN FOR LIPID AND BLOOD GLUCOSE REGULATION

SEQUENCE LISTING

The instant application contains a Sequence Listing which has been submitted electronically in ASCII format and is hereby incorporated by reference in its entirety. Said ASCII copy, created on Mar. 14, 2022, is named 15079_0006-00000_SL.txt and is 45,338 bytes in size.

The present disclosure relates to a GLP-1-FGF21 dual-function protein and related pharmaceutical combination, and also relates to the use of said dual-function protein for preparing a medicament for treating type 2 diabetes, obesity, hyperlipidaemia, fatty liver disease and/or metabolic syndrome, and treatment of these diseases using the medicament.

Glucagon-like peptide-1 (GLP-1) is an endocrine peptide consisting of 36 amino acids secreted by mammalian intestinal L cells, and stimulates insulin secretion from pancreatic beta cells in a glucose dependent manner by binding to and activating GLP-1 receptor (GLP-1R), inhibits glucagon release from pancreatic alpha cells to maintain normal glucose level. In addition, it inhibits gastrointestinal movement and suppresses appetite (Knudsen L B, J Med Chem, 2004, 4128-4134). Native human GLP-1 is easily inactivated in vivo by dipeptidyl peptidase IV (DDP-IV), and has a short circulating half-life. Exendin-4 is isolated from the saliva of toxic lizards from South Africa and has 39 amino acids with 53% homology to human GLP-1 and exerts a similar biological activity. Compared with the human GLP-1, Gly replaces Ala at the second position of N-terminus of Exendin-4 which enhances resistance of the peptide to the proteolytic degradation induced by DDP-IV and extends the circulating half-life in vivo. Exendin-4 has a special Trap-cage structure at the C-terminus, such that its binding affinity with GLP-1 receptor is significantly higher than that of human GLP-1 (Neidigh J W et al., Biochemistry, 2001, 40:13188-13200). At the equimolar concentration, Exendin-4 exhibits a stronger effect on promoting insulin release from pancreatic beta cells. Although there is slight difference in structure and amino sequence, both the blood glucose metabolic regulators have been marketed, wherein most predominant ones are Liraglutide of Novo Nordisk and Exenatide of AstraZeneca. Treatment with Liraglutide or Exenatide 2-3 times daily can effectively control the blood glucose level in type 2 diabetes patients. However, the high injection frequency results in high cost and poor clinical compliance for patients. In order to prolong the in vivo half-life and bioavailability of GLP-1 and Exendin-4 analogs, Fc or HSA fusion technologies have been used for developing long-acting drugs. At present, marketed products are Dulaglutide of Eli Lilly and Albiglutide of GlaxoSmithKline. The most extensively used one in clinic is Dulaglutide, a GLP-1 hIgG4 Fc fusion protein (Dulaglutide), wherein its average half-life is up to 90 hours (Chinese patent CN 1802386 B), its clinical indication is type 2 diabetes, and the recommended dose regimen is subcutaneous injection once a week. Clinical study showed that Dulaglutide could effectively control postprandial blood glucose and glycosylated hemoglobin of diabetic patients, and lower the body weight of obese patients by inhibiting appetite. However, varying degrees of gastrointestinal adverse effects were observed. Epidemiological investigation showed that the large percentage of patients with type 2 diabetes accompanied with nonalcoholic fatty liver disease and lipid metabolism disorder (Radaelli M G et al., J Endocrinol Invest, 2017, s40618). However, no clinical study demonstrated that human GLP-1 or Exendin-4 analogs have the effect of treating fatty liver and hyperlipidaemia independent of weight loss (Petit J M, Diabetes Metab, 2017, 43, 2S28-2S33). Therefore, GLP-1 products cannot completely satisfy all clinical needs for patients with type 2 diabetes.

The family of fibroblast growth factors (FGFs) has 22 members and 7 subfamilies, wherein the FGF19 subfamily exerts physiological activity in an endocrine manner, involves the regulation and control of energy and cholic acid homeostasis, glucose and lipid metabolism, and phosphate and vitamin D homeostasis (Moore D D et al., Science, 2007, 316:1436-1438 and Beenken et al., Nature Reviews Drug Discover, 2009, 8:235). FGF21 is a member of FGF19 subfamily, and has 181 amino acids. The C-terminus of FGF21 binds first to a co-factor O-Klotho transmembrane protein, induces FGFR binding to the N-terminus of FGF21, then forms a stable FGF21β-Klotho/FGFR complex, which trigger subsequent signaling pathway in vivo (Yie J et al., FEBS Lett, 2009, 583(1):19-24 and Micanovic R et al., J Cell Physiol, 2009, 219(2): 227-234). Under physiological conditions, FGF21 is to promote glucose utilization independent of insulin (Kharitonenkov A et al., J Clin Invest, 2005, 115(6): 1627-1635), to enhance insulin sensitization (Duthchak P A et al., Cell, 2012, 148, 387-393), to inhibit de novo lipogenesis and promote the fatty acid β-oxidation in liver, to decrease serum triglyceride level (Xu J et al., Diabetes, 2009, 58, 250-259). In addition, FGF21 could decrease total cholesterol and low density lipoprotein-cholesterol contents in serum by inhibiting liver SREBP-2 synthesis to relieve hypercholesteremia (Lin Z et al., Circulation, 2015, 131, 1861-1871).

In conclusion, FGF21 exerts multiple regulatory functions on metabolic diseases, such as obesity, type 2 diabetes, nonalcoholic fatty liver and hyperlipidaemia. Meanwhile, FGF21 is the only discovered member without any mitogenic effect in this superfamily, which greatly reduces potential carcinogenicity risk in clinical applications (Wu X et al., Proc Natl Acad Sci USA, 2010, 170: 14158-14163). However, due to its unstable physicochemical property, native FGF21 does not possess druggability so far due to the following reasons: (1) native FGF21 protein has pool stability and is easily degraded by proteases in vivo; (2) FGF21 conformation is unstable with ease of aggregation, which increases difficulty in scale-up production; (3) native FGF21 has short circulating half-life, about 0.5-1 h in mice and 2-3 h in Cynomolgus monkeys (Kharitonenkov A et al., J Clin Invest, 2005, 115: 1627-1635). Various long-acting protein-engineering technologies are commonly used for prolonging the in vivo half-life of recombinant FGF21. For example, conjugation of FGF21 and PEG molecule increases the molecular weight, lowers the glomerular filtration rate, and prolongs the in vivo retention time (see WO 2005/091944, WO 2006/050247, WO 2008/121563 and WO 2012/066075); FGF21 fuses to long chain fatty acid (which can binds to serum albumin) (see WO 2010/084169 and WO 2012/010553); preparation of an agonist antibody which specifically binds to FGFR or FGFR/β-klotho complex to mimic the mechanism of FGF21, and to activate FGF/FGFR signaling pathway (see WO 2011/071783, WO 2011/130417, WO 2012/158704 and WO 2012/170438); FGF21 fuses to Fc fragment to improve half-life (see WO 2004/110472, WO 2005/113606, WO 2009/149171, WO 2010/042747, WO 2010/129503, WO 2010/129600, WO 2013/049247, WO 2013/188181 and WO 2016/114633). At present, there is no marketed drug of long-acting FGF21 protein, but there are three long-acting FGF21 candidates in clinic trials, LY2405319 of Eli Lilly, PF-05231023 of Pfizer and BMS986036 of Bristol-Myers Squibb. In the clinical trials, for patients with type 2 diabetes, LY2405319 and PF-05231023 had weight loss effect and decreased serum TG level, but had no positive therapeutic effect on blood glucose (Gaich G et al., Cell Metab, 2013, 18:333-340 and Dong J Q et al., Br J Clin Pharmacol, 2015, 80-1051-1063). BMS986036 exhibited a good therapeutic effect on nonalcoholic fatty liver, but there was no experimental study on blood glucose control for patients with type 2 diabetes. Above-mentioned results showed that although the use of long-acting FGF21 protein alone can exert many pharmacodynamic activities such as in body weight, nonalcoholic fatty liver and hyperlipidaemia. However, it cannot satisfy the blood glucose control requirement which is crucial in the treatment of patients with type 2 diabetes.

Recently, some studies reported that the combination of GLP-1 and FGF21 has a synergistic effect on blood glucose control. For example, CN 102802657 A disclosed that the combination of GLP-1 and FGF21 can synergistically lower the blood glucose level in db/db mice. However, the combined usage of drugs not only increases the administration frequency for patients and reduces the patient compliance, but also greatly increases treatment costs. In addition, a dual-function protein prepared by fusing GLP-1 and FGF21 was also reported. In order to solve the issue that FGF21 is easily degraded in vivo, scientists generally introduce point mutations in native FGF21 molecule, but this inevitably increases the potential immunogenicity of the dual-function protein (WO 2017/074123 and CN 104024273 B). Furthermore, the reported synergistic effect of FGF21 and GLP-1 generally exhibited in terms of blood glucose control, but their synergistic effects in terms of other metabolic diseases, such as obesity, nonalcoholic fatty liver and lipid metabolism disorder are not investigated by comparing with marketed long-acting GLP-1 analogs. The reasons for lack of above-mentioned investigations may comprise the following: (1) neither native GLP-1 nor FGF21 is stable in vivo, and defection of structural integrity and stability in any molecule will eliminate the synergistic effect; (2) in the process of fusion of GLP-1 and FGF21 into a single protein, their respective three-dimensional conformation needs to be maintained to the maximum extent for preventing mutual interference, such that the functional synergy will be achieved, and this should be carefully considered when designing the molecule; (3) the functions of both GLP-1 and FGF21 depend on binding to their respective receptors, and it needs to be confirmed by a number of in vitro and in vivo experiments to clarify the conditions under which the dynamic equilibrium can be achieved among them. So far, there is no such report in published patents or other non-patent documents.

In conclusion, if a GLP-1-FGF21 dual-function protein drug that has enhanced stability, prolonged half-life and low immunogenicity can be developed in the art, then the multiple requirements of patients with type 2 diabetes for reducing blood glucose, relieving hepatic steatosis, reducing body weight and improving metabolic disorders of circulating lipids can be met.

SUMMARY OF THE DISCLOSURE

The present disclosure provides a dual-function protein having a synergistic effect in terms of blood glucose and lipid regulations and comprising human GLP-1 analog and human FGF21, the preparation method therefor and the use thereof. The present disclosure solves the issues such as the defects relating to unstable structure and short in vivo half-life of native GLP-1 or FGF21, retains the strong hypoglycemic effect of GLP-1 and the physiological effects of FGF21 on insulin sensitization, weight loss, fatty liver and hypercholesteremia treatment, and relieves gastrointestinal adverse effects caused by GLP-1 to some extent.

In one embodiment of the present disclosure, a dual-function protein can synergistically regulate blood glucose and lipids, wherein said dual-function protein comprises human glucagon-like peptide-1 analog (abbreviated as GLP-1 analog hereafter), linker peptide 1 (abbreviated as L1 hereafter), human fibroblast growth factor 21 (abbreviated as FGF21 hereafter), linker peptide 2 (abbreviated as L2 hereafter) and human immunoglobulin Fc fragment (abbreviated as Fc fragment hereafter) sequentially from the N-terminus to the C-terminus; wherein the linker peptide 1 comprises a flexible peptide; the linker peptide 2 comprises a flexible peptide and rigid peptide, the rigid peptide comprises at least 1 rigid unit, and the rigid unit comprises carboxyl terminal peptide of human chorionic gonadotropin β-subunit or a truncated sequence thereof.

In one embodiment of the present disclosure, a dual-function protein can synergistically regulate blood glucose and lipids, wherein said dual-function protein consists of sequentially human glucagon-like peptide-1 analog (abbreviated as GLP-1 analog hereafter), linker peptide 1 (abbreviated as L1 hereafter), human fibroblast growth factor 21 (abbreviated as FGF21 hereafter), linker peptide 2 (abbreviated as L2 hereafter) and human immunoglobulin Fc fragment (abbreviated as Fc fragment hereafter) from the N-terminus to the C-terminus; wherein the linker peptide 1 consists of a flexible peptide; the linker peptide 2 consists of a flexible peptide and rigid peptide, the rigid peptide consists of at least 1 rigid unit, and the rigid unit comprises carboxyl terminal peptide of human chorionic gonadotropin β-subunit or a truncated sequence thereof.

In the present disclosure, said "human GLP-1 analog" refers to an analog, fusion peptide, or derivative which are obtained by substituting, deleting or adding one or more amino acid residues on the amino acid sequence of human GLP-1 (as shown in SEQ ID NO: 1) and maintains human GLP-1 activity. For example, said GLP-1 analog comprises but is not limited to the amino acid sequences as shown in SEQ ID NO: 2, 3, 4 or 5 in the sequence listing. All sequences in the sequencing listing are incorporated herein in their entireties. In at least one embodiment of the present disclosure, said GLP-1 analog is shown in SEQ ID NO: 2, and in another embodiment, said GLP-1 analog is shown in SEQ ID NO: 5.

In the present disclosure, said "linker peptide 1 (L1)" is a short peptide between GLP-1 analog and FGF21 and has connecting function. In at least one embodiment, said linker peptide 1 is non-immunogenic, and generates enough distal distance between GLP-1 analog and FGF21, such that minimal steric hindrance effect is present, which does not affect or not affect severely correct folding and spatial conformation of GLP-1 analog and FGF21. A person skilled in the art can design linker peptides according to conventional methods in the art. In at least one embodiment, a flexible peptide comprising 2 or more amino acids is used, and the amino acids are selected from the following amino acids: Gly(G), Ser(S), Ala(A) and Thr(T); in at least one embodiment, said linker peptide 1 comprises G and S residues. The length of the linker peptide is very important for the activity of the dual-function protein, and in at least one embodiment, the linker peptide consists of 5-30 amino acids. In a at least one embodiment of the present disclosure, the amino acid sequence of said linker peptide 1 is GGGGGGGSGGGGSGGGGS (SEQ ID NO: 16).

In the present disclosure, said "FGF21" comprises the sequence as shown in SEQ ID NO: 6 in which the secreting leader signal of amino acid position 1-28 is deleted; or comprises the isoform sequence of SEQ ID NO: 6 in which the secreting leader signal of amino acid position 1-28 is deleted and which has G141S or L174P substitution. In a at least one embodiment of the present disclosure, said FGF21 comprises the amino acid sequence as shown in SEQ ID NO: 6 in which the secreting leader signal of amino acid position 1-28 is deleted and has L174P substitution.

In the present disclosure, said "linker peptide 2 (L2)" is a short peptide between FGF21 and Fc fragment and having connect function. Said linker peptide consists of a flexible peptide and a rigid peptide, wherein said flexible peptide comprises 2 or more amino acid residues which are selected from Gly(G), Ser(S), Ala(A) and Thr(T). In at least one embodiment, said flexible peptide comprises G and S residues. With regard to the present disclosure, preferably, the general structural formula of the amino acid composition of said flexible peptide is (GS)a(GGS)b(GGGS)c(GGGGS)d (SEQ ID NO: 17), wherein a, b, c and d are integers greater than or equal to 0, and a+b+c+d ≥1.

In some embodiments of the present disclosure, said flexible peptide comprised in said L2 is selected from the following sequences:

```
                                    (SEQ ID NO: 18)
    (i)   GGGGS;

(SEQ ID NO: 19)
    (ii)  GSGGGSGGGGSGGGGS;

(SEQ ID NO: 20)
    (iii) GSGGGGSGGGGSGGGGSGGGGSGGGGS;

(SEQ ID NO: 21)
    (iv)  GGGGSGGGGSGGGGSGGGGSGGGGSGGGGSGGGGS;

(SEQ ID NO: 22)
    (v)   GGGSGGGSGGGSGGGSGGGS;

(SEQ ID NO: 23)
    (vi)  GGSGGSGGSGGS.
```

In the present disclosure, said rigid peptide constituting said linker peptide 2 (L2) consists of one or more rigid units, and said rigid units are selected from a full-length or truncated sequence consisting of carboxyl terminal amino acids 113 to 145 of human chorionic gonadotropin β-subunit (known as CTP rigid unit hereafter); specifically, said CTP rigid unit comprises the amino acid sequence as shown in SEQ ID NO: 7 or the truncated sequences thereof.

In at least one embodiment, said CTP rigid unit comprises at least 2 glycosylation sites; for example, in one at least one embodiment of the present disclosure, said CTP rigid unit comprises 2 glycosylation sites, for example, said CTP rigid unit comprises 10 amino acids of N-terminus of SEQ ID NO: 7, i.e. SSSS*KAPPPS* (SEQ ID NO: 35); or said CTP rigid unit comprises 14 amino acids of C-terminus of SEQ ID NO: 7, i.e. S*RLPGPS*DTPILPQ (SEQ ID NO: 36); for another example, in another embodiment, said CTP rigid unit comprises 3 glycosylation sites, for example, said CTP rigid unit comprises 16 amino acids of N-terminus of SEQ ID NO: 7, i.e. SSSS*KAPPPS*LPSPS*R (SEQ ID NO: 37); for another example, in another embodiment, said CTP rigid unit comprises 4 glycosylation sites, for example, said CTP rigid unit comprises 28, 29, 30, 31, 32 or 33 amino acids and starts at positions 113, 114, 115, 116, 117 or 118 and terminates at position 145 of human chorionic gonadotropin β-subunit. Specifically, said CTP rigid unit comprises 28 amino acids of N-terminus of SEQ ID NO: 7, i.e. SSSS*KAPPPS*LPSPS*RLPGPS*DTPILPQ (SEQ ID NO: 38). In the present disclosure, * represents glycosylation sites. All possibilities represent independent embodiments of the present disclosure.

In some embodiments, the CTP rigid unit comprised in L2 of the present disclosure can preferably comprise one of the following sequences:

```
                                            (SEQ ID NO: 27)
    (i)   CTP¹: SSSSKAPPPSLPSPSRLPGPSDTPILPQ;

(SEQ ID NO: 7)
    (ii)  CTP²: PRFQDSSSSKAPPPSLPSPSRLPGPSDTPILPQ;

(SEQ ID NO: 24)
    (iii) CTP³: SSSSKAPPPS;

(SEQ ID NO: 25)
    (iv)  CTP⁴: SRLPGPSDTPILPQ;

(SEQ ID NO: 26)
    (v)   CTP⁵: SSSSKAPPPSLPSPSR.
```

In some embodiments, the CTP rigid unit provided in the present disclosure has at least 70% homology to the native CTP amino acid sequence; In some embodiments, the CTP rigid unit provided in the present disclosure has at least 80% homology to the native CTP amino acid sequence; In some embodiments, the CTP rigid unit provided in the present disclosure has at least 90% homology to the native CTP amino acid sequence; In some embodiments, the CTP rigid unit provided in the present disclosure has at least 95% homology to the native CTP amino acid sequence.

In some embodiments of the present disclosure, L2 comprises 2, 3, 4 or 5 above-mentioned CTP rigid units. In some embodiments of the present disclosure, L2 of said dual-function protein comprises 2 $CTP^3$ rigid unit: SSSSKAPPPSSSSSKAPPPS (SEQ ID NO: 28) ($CTP^3$-$CTP^3$, or represented as $(CTP^3)_2$).

In the present disclosure, said "Fc fragment" is selected from the Fc fragments of human immunoglobulins IgG, IgM, IgA and variants thereof, in at least one embodiment, is selected from the Fc fragments of human IgG1, IgG2, IgG3 or IgG4 and variants thereof, wherein said human IgG Fc fragment (represented as vFc) comprises at least one amino acid modification located in wild type human IgG Fc, and the Fc variants have non-lytic characteristics, and show an extremely minimal Fc-mediated effector functions (ADCC and CDC functions) and/or enhanced binding affinity with FcRn receptor; most preferably, human IgG Fc variant is selected from the group of:

(i) vFcγ1: hinge, CH2 and CH3 regions of human IgG1 containing Leu234Val, Leu235Ala and Pro331Ser mutations (the amino acid sequence as shown in SEQ ID NO: 8);

(ii) vFcγ2-1: hinge, CH2 and CH3 regions of human IgG2 containing Pro331Ser mutation (the amino acid sequence as shown in SEQ ID NO: 9);

(iii) vFcγ2-2: hinge, CH2 and CH3 regions of human IgG2 containing Thr250Gln and Met428Leu mutations (the amino acid sequence as shown in SEQ ID NO: 10);

(iv) vFcγ2-3: hinge, CH2 and CH3 regions of human IgG2 containing Pro331Ser, Thr250Gln and Met428Leu mutations (the amino acid sequence as shown in SEQ ID NO: 11).

(v) vFcγ4: hinge, CH2 and CH3 regions of human IgG4 containing Ser228Pro and Leu235Ala mutations (the amino acid sequence as shown in SEQ ID NO: 12).

The Fc variants provided by the present disclosure comprises, but is not limited to above 5 variants of (i) to (v), and also can be the combination or overlap of functional variants among same IgG subtypes, for example, the variant of above-mentioned (iv) is a new combination variant of IgG2 Fc obtained by overlapping the mutation sites in (ii) and (iii).

The Fc variant (vFc) in the dual-function protein of the present disclosure contains human IgG, such as the hinge region and CH2 and CH3 regions of human IgG1, IgG2 and IgG4. Such CH2 region contains amino acid mutations at positions 228, 234, 235 and 331 (determined by EU numbering system). It is believed that these amino acid mutations can reduce Fc effector function. Human IgG2 does not bind to FcγR, but shows a very weak complement activity. The complement activity of Fcγ2 variant having Pro331Ser mutation should be lower than that of native Fcγ2, and is still an FcγR non-binder. IgG4 Fc has some defects in activation of complement cascade, and its binding affinity with FcγR is lower than that of IgG1 by about one order of magnitude. Compared with native Fcγ4, the Fcγ4 variant having Ser228Pro and Leu235Ala mutations should show the minimal effector function. Compared with native Fcγ1, Fcγ1 having Leu234Val, Leu235Ala and Pro331Ser mutations also shows a reduced effector function. These Fc variants are more suitable for preparing a dual-function protein of FGF21 and analogs thereof than native human IgG Fc. However, positions 250 and 428 (positions determined by EU numbering system) contain amino acid substitutions, such that the binding affinity of Fc region with neonate receptor FcRn is increased, thus further prolonging the half-life (Paul R et al., J Biol Chem, 2004, 279:6213-6216); the combination or overlap of above-mentioned two types of functional variants obtains new variants which have reduced effector function and prolonged half-life. The Fc variants of the present disclosure comprises, but is not limited to above-mentioned mutations; the substitutions at other sites can also be introduced, such that Fc has a reduced effector function and/or enhanced affinity with FcRn receptor, at the same time, without causing reduced functions/activities of Fc variants or adverse conformational changes, and see Shields R L et al., J Biol Chem, 2001, 276(9):6591-604 for common mutation sites.

In one at least one embodiment of the present disclosure, the amino acid sequence of said dual-function protein is shown in SEQ ID NO: 13. In another at least one embodiment of the present disclosure, the amino acid sequence of said dual-function protein is shown in SEQ ID NO: 15.

The dual-function protein of the present disclosure is glycosylated; preferably, said dual-function protein is glycosylated by being expressed in mammalian cells; in at least one embodiment, said dual-function protein is glycosylated by being expressed in Chinese hamster ovary cells.

According to another embodiment of the present disclosure, provided is a DNA encoding the above-mentioned dual function protein. In one at least one embodiment of the present disclosure, the DNA sequence encoding said dual-function protein is shown in SEQ ID NO: 14.

According to still another embodiment of the present disclosure, provided is a vector. The vector comprises the above-mentioned DNA.

According to still another embodiment of the present disclosure, provided is a host cell. The host cell comprises the above-mentioned vector, or is transfected with the above-mentioned vector.

In a particular embodiment of the present disclosure, the host cell is a CHO-derived cell strain DXB-11.

According to still another embodiment of the present disclosure, provided is a pharmaceutical composition. The pharmaceutical composition comprises a pharmaceutically acceptable carrier, excipient or diluent, and an effective amount of the above-mentioned synergistic dual function protein.

According to another embodiment of the present disclosure, provided is a method for preparing or producing said dual-function protein from mammalian cell lines (such as a CHO-derived cell line), comprising following steps:
(a) introducing a DNA encoding the above-mentioned dual-function protein into a mammalian cell;
(b) screening a high-yield cell strain expressing more than 20 pg/$10^6$ cells within a period of every 24 hours in the growth medium thereof from step (a);
(c) culturing the screened cell strain in step (b);
(d) harvesting the fermentation broth obtained from step (c), and purifying the dual function protein.

In at least one embodiment, said mammalian cell in step (a) is CHO cell; in at least one embodiment, said mammalian cell in step (a) is CHO-derived cell line DXB-11.

According to still another embodiment of the present disclosure, provided is the use of said dual-function protein in the preparation of a drug for treating FGF21 related diseases and GLP-1 related diseases, and other metabolic, endocrinic and cardiovascular diseases, comprising obesity, types 1 and 2 diabetes, pancreatitis, dyslipidemia, nonalcoholic fatty liver disease, nonalcoholic steatohepatitis, insulin tolerance, hyperinsulinemia, glucose intolerance, hyperglycemia, metabolic syndrome, acute myocardial infarction, high blood pressure, cardiovascular disease, atherosclerosis, peripheral arterial disease, stroke, cardiac failure, coronary heart disease, nephropathy, diabetic complication, neuropathy, gastroparesis, and conditions associated with the severe inactivation mutations of insulin receptor; preferably, said diseases comprise obesity, types 1 and 2 diabetes, dyslipidemia, nonalcoholic fatty liver disease, nonalcoholic steatohepatitis and metabolic syndrome.

Compared with existing products, the dual-function protein of the present disclosure has many advantages, which are demonstrated in detail by using, e.g., dual-function protein FP4I-2 of the present disclosure:

1. The half-life in vivo is prolonged, and blood glucose-lowering activity in vivo is maintained for a longer period of time. The glucose tolerance test performed on C57BL/6 mice shows that at 144 h after a single dose of FP4I-2, FP4I-2 still exhibits a good ability for promoting glucose utilization, which is better than the commercially available GLP-1 analog Liraglutide and Exenatide and native FGF21. Compared with GLP-1-Fc fusion protein Dulaglutide, FP4I-2 exhibits a more excellent blood glucose control effect in the type 2 diabetes mice.

2. Improved safety and tolerability. Dulaglutide induces severe gastrointestinal adverse effects after the first administration. In db/db mice, the initial 24 hour food intake of the mice after first administration of FP4I-2 is significantly elevated relative to that of mice administrated with Dulaglutide, which shows that the dual-function protein FP4I-2 can effectively relieve appetite inhibition induced by gastrointestinal adverse effects.

3. Improved therapeutic effects of dual-function protein on fatty liver. Compared with Dulaglutide, FP4I-2 can significantly reduce the liver mass of db/db mice, improve liver function, and the mechanism does not completely depend on the appetite inhibition related to GLP-1analog, demonstrating the physiological activity of FGF21. Relative to native FGF21, the in vivo half-life of FP4I-2 is significantly prolonged. In the animal model, the dose frequency of FP4I-2 is twice per week, which will improve the clinical feasibility.

4. The C-terminal sequence of FGF21 is crucial to its activity, most dual-proteins reported in the prior art uses FGF21 N-terminal fusion, and free C-terminus is beneficial to maintain activity; however, the C-terminus of FGF21 also contains various protease hydrolysis sites, and is very easily degraded; exposed intact C-terminus is more easily attacked by protease and degraded. In order to overcome this problem, the prior art avoids using native FGF21, but introducing corresponding mutations to improve its stability, however, this inevitably increases the potential immunogenicity of dual-function proteins. In contrast, the dual-function protein constructed in the present disclosure uses native FGF21, and has an Fc fragment connected at its C-terminus. The dual-function protein provided by the present disclosure not only has a significantly prolonged in vivo half-life in circulation, but also has a synergistic effect in terms of blood glucose and lipid regulations, which suggests that the constructed dual-function protein well maintains the properties of this two active molecules, and has good stability. This benefits result from the new type of linker peptide among FGF21 and Fc variants; the linker peptide consists of a flexible peptide and a rigid peptide, and the CTP rigid unit contains multiple O-carbohydrate side chains, can forms a relatively stable three-dimensional conformation, which can effectively separate FGF21 and Fc, thereby lowers the steric hindrance effect caused by Fc fragment to the utmost extent and keep relatively good FGF21 biological activity. In addition, carbohydrate side chain of CTP rigid unit can mask the enzymolysis site of FGF21. The protective effect lowers the sensibility of enzymolysis to proteases and achieves the purpose for protein stability.

5. Mutations on Fc only retains the long half-life property in circulation of Fc, reducing or eliminating ADCC and CDC effects (such as P331S), thus increases the safety of drug use. In addition, Fc variants (such as T250Q/M428L) having an enhanced binding affinity with neonate receptor (FcRn) can further prolong the half-life of dual function protein.

DETAILED DESCRIPTION OF THE DISCLOSURE

Human GLP-1 Analog

The term "human GLP-1 analog" used herein refers to an analog, fusion peptide, and derivative which are obtained by substituting, deleting or adding one or more amino acid residues on the amino acid sequence of human GLP-1 (as shown in SEQ ID NO: 1) and maintain human GLP-1 activity. For example, said human GLP-1 analog comprises but are not limited to the amino acid sequences as shown in SEQ ID NO: 2, 3, 4 or 5 in the sequence listing.

Human FGF21

The term "human FGF21" used herein refers to a wild type human FGF21 polypeptide.

The sequence of the wild type FGF21 protein can be obtained from UNIPROT database, and the accession number is Q9NSA1. The precursor protein consists of 209 amino acids, comprising a signal peptide (amino acids 1-28) and a mature protein (amino acids 29-209).

US 2001012628 A1 teaches the isoform or allelic form of the wild type FGF21 having the substitution from Leu to Pro in the mature protein (in the present disclosure, as shown in positions 47-227 of SEQ ID NO: 13); another isoform of wild type FGF21 having the substitution from Gly to Ser (Gly at the position 141 of SEQ ID NO: 6 is substituted or replaced by Ser).

WO 2003/011213 teaches another isoform (see SEQ ID NO: 2 disclosed in WO 2003/011213, which has a signal peptide of 27 amino acid residues) having a relatively short signal peptide (in the present disclosure, Leu at position 23 of SEQ ID NO: 6 deleted).

In the present disclosure, the wild type FGF21 comprises SEQ ID NO: 6 and the sequence of the mature protein portion (amino acids 29-209) of the isoform having L174P or G141S substitutions after removing the leader peptide; in addition, also comprised is the full-length sequence of the precursor protein with the above-mentioned 27 or 28 amino acid signal peptide added before those above sequences.

hCG-β Carboxyl Terminal Peptide (CTP)

CTP is a short carboxyl terminal peptide of human chorionic gonadotropin (hCG) β-subunit. Four reproduction-related polypeptide hormones follicle-stimulating hormone (FSH), luteinizing hormone (LH), thyroid stimulating hormone (TSH) and chorionic gonadotropin (hCG) contain the same alpha subunit and the different specific beta subunit from each other. The in vivo half-life of hCG, compared with other three hormones, is prolonged, which is mainly due to the specific carboxyl terminal peptide (CTP) of its beta subunit (Fares F A et al., Proc Natl Acad Sci USA, 1992, 89: 4304-4308). Native CTP contains 37 amino acid residues, has 4 O-glycosylation sites, and has sialic acid residue at the terminus. Negative charged, highly sialylated CTP can resist the clearance of kidneys on same, thus prolong the in vivo half-life of same. However, the inventors herein creatively connects a rigid peptide including at least one CTP rigid unit with a flexible peptide with a suitable length, collectively as linker peptide 2 for connecting FGF21 and Fc fragment.

N-terminal and C-terminal sequences of FGF21 are crucial to the functions of FGF21. The spatial conformation of FGF21 is complex and fragile, such that FGF21 has a poor stability, is easily degraded and aggregated; if FGF21 is fused to a ligand, the steric hindrance effect will interfere with the correct folding of FGF21, making the activity of FGF21 significantly lowered or even lost, or more easily to generate a polymer. Adding CTP rigid units between FGF21 and Fc variants is equivalent to adding a section of rigid linker peptide. In one embodiment, it ensures that the FGF21 fused at N-terminus will not affect the binding site of Fc variants and FcRn, thereby not affecting the half-life; in addition, the Protein A binding site of Fc is very important for the purification step in the preparation process, and connecting CTP rigid units ensures that N-terminus fused FGF21 also will not "mask" its binding site with protein A. In another embodiment, the addition of CTP rigid units also makes Fc fragments with about 25 KD not interfere with the correct folding of N-terminus fused FGF21, and not cause the biological activity/functions of FGF21 lowered or lost. This may be interpreted that a CTP rigid polypeptide with multiple carbohydrate side chains, which, relative to the random coil of (GGGGS)n (SEQ ID NO: 29) of flexible linker peptides, can form a stable three-dimensional conformation, and this "barrier" effect promotes FGF21 and Fc fragment to fold and form a correct three-dimensional conformation independently, thus not affecting their respective biological activity. In another embodiment, the protective effect of carbohydrate side chain of CTP can lower the sensibility of linker peptides to proteases, such that the dual-function protein is not easily degraded in the linker region. In addition, CTP is derived from native human hCG, has no immunogenicity, therefore, relative to non-native encoded amino acid sequence, is more suitable for being used as a linker peptide.

IgG Fc Variant

Non-Lytic Fc Variants

Fc elements are derived from the constant region Fc of immunoglobulin IgG, and have an important effect in immune defense for eliminating pathogens. The effector function of IgG mediated by Fc is exerted via two mechanisms: (1) binding to the Fc receptors (FcγRs) on the cell surface, digesting pathogens by phagocytosis or lysis, or by killer cells through antibody-dependent cytotoxic (ADCC) pathway, or (2) binding to C1q of the first complement component C1, triggering the complement dependent cytotoxic (CDC) pathway, thereby lysing pathogens. Among four human IgG subtypes, IgG1 and IgG3 can effectively bind to FcγRs, the binding affinity of IgG4 with FcγRs is relatively low, and the binding of IgG2 with FcγRs is too low to be determined, and therefore, human IgG2 almost has no ADCC effect. In addition, human IgG1 and IgG3 also can effectively bind to C1q, thereby activating the complement cascade. The binding of human IgG2 with C1q is relatively weak, and IgG4 does not bind with C1q (Jefferis R et al., Immunol Rev, 1998, 163: 59-76), and therefore, the CDC effect of human IgG2 is also weak. There is no native IgG subtype which is very suitable for constructing GLP-1-FGF21 dual function protein. In order to obtain a non-lytic Fc without effector function, the most effective method is performing mutation modification on the complement and receptor binding domain of Fc fragment, regulating the binding affinity of Fc with related receptors, reducing or eliminating ADCC and CDC effects, only retaining the long half-life property of Fc in circulation, and not generating cytotoxicity. For additional mutation sites comprised in non-lytic Fc variants, one can refer to R L et al., J Biol Chem, 2001, 276(9):6591-604 or Chinese invention patent CN 201280031137.2.

Fc Variants Having an Enhanced Binding Affinity with Neonate Receptor (FcRn)

The plasma half-life of IgG depends on its binding with FcRn, and generally, they bind at pH 6.0, and dissociate at pH 7.4 (plasma pH). By the study of the binding site of the two, the binding site on IgG with FcRn is modified, such that the binding ability thereof is increased at pH 6.0. It is proven that the mutations of some residues in human Fcγ domain which is important for binding with FcRn can increase the serum half-life. It has been reported that the mutations of T250, M252, S254, T256, V308, E380, M428 and N434 can increase or reduce FcRn binding affinity (Roopenian et al., Nat Rview Immunology, 2007, 7:715-725). South Korea patent no. KR 10-1027427 discloses Trastuzumab (Herceptin, Genentech) variants with an increased FcRn binding affinity, and these variants comprise one or more amino acid modifications selected from 257C, 257M, 257L, 257N, 257Y, 279Q, 279Y, 308F and 308Y. South Korea patent no. KR 2010-0099179 provides bevacizumab (avastin, Genentech) variants, and these variants comprise amino acid modifications of N434S, M252Y/M428L, M252Y/N434S and M428L/N434S, and show an increased half-life in vivo. In addition, Hinton et al. also find that 2 mutants of T250Q and M428L can increase the binding with FcRn by 3 and 7 times respectively. Mutating the 2 sites at the same time, the binding will be increased by 28 times. In rhesus monkeys, the mutants of M428L or T250QM/428L show the plasma half-life in vivo is increased by 2 times (Paul R. Hinton et al., J Immunol, 2006, 176:346-356). For additional mutation sites comprised in Fc variants having an enhanced binding affinity with neonate receptor (FcRn), one can refer to Chinese invention patent CN 201280066663.2. In addition, in some studies performing T250Q/M428L mutations on the Fc fragment of five humanized antibodies, the interaction between Fc and FcRn is improved, and in the subsequent in vivo pharmacokinetic test, it finds that using subcutaneous injection administration, the pharmacokinetic parameters of Fc mutation antibodies are improved compared with wild type antibodies, such as an increased in vivo exposure, lowered clearance rate and improved subcutaneous bioavailability (Datta-Mannan A et al., MAbs. Taylor & Francis, 2012, 4(2): 267-273).

Terms "FGF21-related conditions" and "GLP-1-related conditions" comprise obesity, types 1 and 2 diabetes, pancreatitis, dyslipidemia, nonalcoholic fatty liver disease, non-alcoholic steatohepatitis, insulin tolerance, hyperinsulinemia, glucose intolerance, hyperglycemia, metabolic syndrome, acute myocardial infarction, high blood pressure, cardiovascular disease, atherosclerosis, peripheral arterial disease, stroke, cardiac failure, coronary heart disease, nephropathy, diabetic complication, neuropathy, gastroparesis, and conditions associated with the severe inactivation mutations of insulin receptor.

"Conditions associated with the severe inactivation mutations of insulin receptor" describe the conditions of subjects with insulin receptor (or a direct downstream possible protein thereof) mutation, wherein said mutation results in a severe insulin tolerance, but generally no obesity which is common in type 2 diabetes. In many embodiments, subjects with these conditions exhibit the symptom complex of types 1 and 2 diabetes. Therefore, the involved subjects are divided into several types according to the severity, comprising: type A diabetes resistance, type C insulin resistance (AKA HAIR-AN syndrome), Rabson-Mendenhall syndrome, Donohue's syndrome or Leprechaunism. These conditions are associated with a very high endogenous insulin level, and results in an elevated blood glucose level. Therefore, in the involved subjects, there are many clinical features associated with "insulin toxicity", wherein the clinical features comprise androgen excess, polycystic ovarian syndrome (PCOS), hirsutism and acanthosis nigricans (overgrowth of wrinkly skin and pigmentation).

"Diabetic complications" is the dysfunction of other tissue/organs of the body induced by chronic hyperglycemia, such as diabetic nephropathy, diabetic neuropathy, diabetic feet (foot ulcers and low blood circulation) and eye lesions (retinopathy). Diabetes also increases the risks of heart disease and osteoarticular diseases. The other long-term complications of diabetes comprise skin, digestive, sexual function, teeth and gums disease.

"Metabolic syndrome (MS)" is the morbidness caused by abnormal metabolic parameters, comprising: (1) abdominal obesity or overweight; (2) atherosclerosis and dyslipidemia, such as hypertriglyceride and reduction in high density lipoprotein cholesterol (HDL-C); (3) hypertension; (4) insulin resistance and/or abnormal glucose tolerance. In some criteria, microalbuminuria, hyperuricemia, pro-inflammatory state (C-reactive protein) and pro-thrombogenesis state (increase in Fibrinogen and Plasminogen inhibitor-1) are also comprised.

"Dyslipidemia" is a lipoprotein metabolic disorder, comprising the oversynthesis or defect of lipoprotein. Dyslipidemia can exhibit as the elevated concentration of total cholesterol, low density lipoprotein (LDL) cholesterol and triglycerides, and the reduced concentration of high density lipoprotein (HDL) cholesterol.

"Nonalcoholic fatty liver disease (NAFLD)" is a liver disease which is not associated with abused alcohol consumption and is characterized in hepatocellular steatosis.

"Nonalcoholic steatohepatitis (NASH)" is a liver disease which is not associated with abused alcohol consumption and is characterized in hepatocellular steatosis accompanied by lobular inflammation and fibrosis.

"Atherosclerosis" is an angiopathy and is characterized in lipid deposits irregularly distributed on endangium of large and medium-sized arteries, which results in hemadostenosis, and eventually develops into fibrosis and calcification.

BRIEF DESCRIPTION OF THE DRAWINGS

FIG. 1. shows the nucleotide sequence of dual-function protein FP4I-2 of SpeI/EcoRI fragment in PCDNA3.1 expression vector according to the embodiments of the present disclosure and the deduced amino acid sequence, consisting of alpha 1 microglobulin leader peptide (1-19), GLP-1 analog (20-47), L1 (48-65), FGF21 mature protein (66-246), L2 (247-301) and IgG2 Fc (302-524). FIG. 1 discloses SEQ ID NOs 33 and 34, respectively, in order of appearance.

Figure 2A:
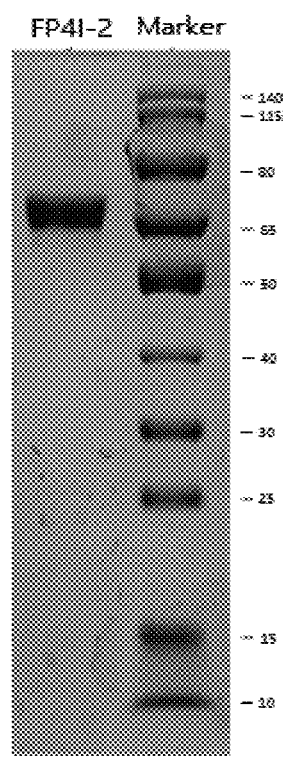
FIG. 2a. Reduced SDS-PAGE electrophoretogram of GLP-1-FGF21 dual-function protein FP4I-2.

The present disclosure is further described below in combination with specific embodiments. It is to be understood that these embodiments serve only to illustrate the present disclosure and are not limiting the scope of the present disclosure. In the following embodiments, experimental methods without specifying specific conditions are generally performed under conventional conditions, for example, those described in Sambrook et al., Molecular Cloning: A Laboratory Manual (New York: Cold Spring Harbor Laboratory Press, 1989), or the conditions recommended by the manufacturer.

Generally, the dual-function protein of the present disclosure is prepared synthetically. The nucleotide sequence according to the present disclosure, a person skilled in the art can conveniently use various known methods to prepare the encoding nucleic acid of the present disclosure. These methods are for example but not limited to: PCR, and DNA artificial synthesis etc., the specific methods can refer to J. Sambrook, "Molecular Cloning: A Laboratory Manual". As an embodiment of the present disclosure, a method comprising fragment synthesis of nucleotide sequences, followed by overlap extension of PCR can be used for constructing the encoding nucleic acid sequence of the present disclosure.

Also provided in the present disclosure is an expression vector comprising a sequence encoding the dual-function protein of the present disclosure and a regulatory element transcriptionally linked thereto. Said "transcriptionally linked" or "transcriptionally linked to" refer to such a condition that some parts of a linear DNA sequence can regulate or control the activity of other parts in the same linear DNA sequence. For example, if a promoter controls the transcription of a sequence, then the promoter is transcriptionally linked to the encoding sequence.

The expression vector can use commercially available ones, for example but not limited to: vectors pcDNA3, pIRES, pDR and pUC18 which can be used for expression in an eukaryotic system. A person skilled in the art can select a suitable expression vector according to the host cell.

According to the restriction map of the known expression vector, a person skilled in the art can insert the sequence encoding the dual-function protein of the present disclosure into a suitable restriction site to prepare the recombinant expression vector of the present disclosure following conventional methods via restriction digestion and ligation.

Also provided in the present disclosure is a host cell expressing the dual-function protein of the present disclosure, wherein said host cell comprises the sequence encoding the dual-function protein of the present disclosure. In at least one embodiment, said host cell is a eukaryotic cell, for example but not limited to CHO, a COS cell, a 293 cell and a RSF cell etc. As a at least one embodiment of the present disclosure, said cell is a CHO cell, which can well express the dual-function protein of the present disclosure, and the dual-function protein with a good binding activity and stability can be obtained.

Also provided in the present disclosure is a method for preparing the dual-function protein of the present disclosure using recombinant DNA, the steps thereof comprise:
 1) Providing a nucleic acid sequence encoding the synergistic dual function protein;
 2) Inserting the nucleic acid sequence of 1) into a suitable expression vector, and obtaining a recombinant expression plasmid;
 3) Introducing the recombinant expression plasmid of 2) into a suitable host cell;
 4) Culturing the transformed host cell under a condition suitable for expression;
 5) Collecting the supernatant, and purifying the dual-function protein product.

To introduce said encoding sequence into the host cell one can use multiple known technologies in the art, for example but not limited to: calcium phosphate precipitation, protoplast fusion, liposome transfection, electroporation, microinjection, reverse transcription method, phage transduction method, and alkali metal ion method.

With respect to the culture of and expression in the host cell can refer to Olander RM Dev Biol Stand, 1996, 86:338. Cells and debris in the suspension can be removed by centrifugation, and the supernatant is collected. Agarose gel electrophoresis technique can be used for identification.

The dual-function protein prepared as described herein can be purified to have a substantially homogeneous property, such as has a single band on SDS-PAGE electrophoresis. For example, when the recombinant protein is expressed for secretion, a commercially available ultrafiltration membrane (such as products of Millipore and Pellicon etc.) can be used to separate said protein, wherein firstly, the expression supernatant is concentrated. The concentrate can be purified by the method of gel chromatography, or by the method of ion exchange chromatography, for example, by anion exchange chromatography (DEAE etc.) or cation exchange chromatography. The gel matrix can be common matrices for protein purification, such as agarose, glucan, and polyamide etc. Q- or SP-groups is a relatively ideal ion exchange group. Finally, the above-mentioned purified product can be further refined and purified by the methods of hydroxyapatite adsorption chromatography, metal chelate chromatography, hydrophobic interaction chromatography and reversed high performance liquid chromatography (RP-HPLC). All the above-mentioned purification steps can be used in different combination in order to make the protein purity substantially homogeneous.

The expressed dual-function protein can be purified using an affinity column containing a specific antibody, receptor or ligand of said dual function protein. According to the properties of the affinity column, conventional methods, such as high salt buffer and changing pH etc. can used to elute the fusion polypeptide binding to the affinity column. Optionally, at the amino terminus or carboxyl terminus of said dual function protein, one or more polypeptide fragments also can be contained as protein tags. Any suitable tags can be used in the present disclosure. For example, said tags can be FLAG, HA, HA1, c-Myc, 6-His (SEQ ID NO: 30) or 8-His (SEQ ID NO: 31) etc. These tags can be used for purifying the dual function protein.

Non-Limiting Exemplary Embodiments

1. A dual-function protein comprising sequentially human GLP-1 analog, linker peptide 1, human FGF21, linker peptide 2 and human immunoglobulin Fc fragment from the N to C-terminus; wherein the linker peptide 1 comprises or consists of a flexible peptide; the linker peptide 2 comprises or consists of a flexible peptide and a rigid peptide, the rigid peptide comprises or consists of at least 1 rigid unit, and the rigid unit comprises a full-length or truncated sequence consisting of carboxyl terminal amino acids 113 to 145 of human chorionic gonadotropin β-subunit.

2. The dual-function protein of embodiment 1, wherein said dual-function protein is glycosylated; preferably, said dual-function protein is glycosylated by being expressed in mammalian cells; and more preferably, said dual-function protein is glycosylated by being expressed in Chinese hamster ovary cells.

3. The dual-function protein of embodiment 1, wherein said human GLP-1 analog is an analog, fusion peptide, or derivative thereof which is obtained by substituting, deleting or adding one or more amino acid residues on the amino acid sequence of SEQ ID NO: 1 and can maintain human GLP-1 activity.

4. The dual-function protein of embodiment 3, wherein the GLP-1 analog comprises an amino acid sequence of SEQ ID NO: 2, 3, 4 or 5.

5. The dual-function protein of embodiment 1, wherein said linker peptide 1 comprises a flexible peptide consisting of 2 or more amino acids; preferably, consisting of 5-30 amino acids.

6. The dual-function protein of embodiment 5, wherein the amino acids of said linker peptide 1 are selected from the following amino acids: G, S, A and T; more preferably, said linker peptide 1 comprises G and S residues; and most preferably, the amino acid sequence of said linker peptide 1 is GGGGGGGSGGGGSGGGGS (SEQ ID NO: 16).

7. The dual-function protein of embodiment 1, wherein said human FGF21 comprises the sequence as shown in SEQ ID NO: 6 in which the leader peptide of amino acid position 1-28 is deleted; or comprises the isoform sequence of SEQ ID NO: 6 in which the leader peptide of amino acid position 1-28 is deleted and which has G141S or L174P substitution.

8. The dual-function protein of embodiment 1, wherein the flexible peptide constituting said linker peptide 2 comprises 2 or more amino acids selected from G, S, A and T; preferably, the general structural formula of the amino acid composition of said flexible peptide is (GS)a(GGS)b(GGGS)c(GGGGS)a (SEQ ID NO: 17), wherein a, b, c and d are integers greater than or equal to 0, and a +b+c+d≥1; more preferably, the amino acid composition of said flexible peptide is selected from:

(i) GGGGS; (SEQ ID NO: 18)

(ii) GSGGGSGGGGSGGGGS; (SEQ ID NO: 19)

(iii) GSGGGGSGGGGSGGGGSGGGGSGGGGS; (SEQ ID NO: 20)

(iv) GGGGSGGGGSGGGGSGGGGSGGGGSGGGGSGGGGS; (SEQ ID NO: 21)

(v) GGGSGGGSGGGSGGGSGGGS; and (SEQ ID NO: 22)

(vi) GGSGGGSGGSGGS. (SEQ ID NO: 23)

9. The dual-function protein of embodiment 1, wherein the rigid units constituting said linker peptide 2 are selected from SEQ ID NO: 7 and the truncated amino acid sequences thereof, wherein said truncated amino acid sequences comprise at least 2 glycosylation sites; preferably, said rigid units comprise one of the following amino acid sequences:

(i) SSSSKAPPPSLPSPSRLPGPSDTPILPQ; (SEQ ID NO: 27)

(ii) PRFQDSSSSKAPPPSLPSPSRLPGPSDTPILPQ; (SEQ ID NO: 7)

(iii) SSSSKAPPPS; (SEQ ID NO: 24)

(iv) SRLPGPSDTPILPQ; or (SEQ ID NO: 25)

(v) SSSSKAPPPSLPSPSR. (SEQ ID NO: 26)

10. The dual-function protein of embodiment 9, wherein said rigid units have at least 90% or 95% identity to the amino acid sequences of the rigid units of embodiment 9.

11. The dual-function protein of embodiment 1, wherein said rigid peptide comprises 1, 2, 3, 4 or 5 rigid units.

12. The dual-function protein of embodiment 1, wherein said human immunoglobulin Fc fragment is a variant having a reduced ADCC effect and/or CDC effect and/or enhanced binding affinity with FcRn receptor; preferably, said Fc variant is selected from:
  (i) hinge, CH2 and CH3 regions of human IgG1 containing Leu234Val, Leu235Ala and Pro331Ser mutations;
  (ii) hinge, CH2 and CH3 regions of human IgG2 containing Pro331Ser mutation;
  (iii) hinge, CH2 and CH3 regions of human IgG2 containing Thr250Gln and Met428Leu mutations;
  (iv) hinge, CH2 and CH3 regions of human IgG2 containing Pro331Ser, Thr250Gln and Met428Leu mutations; and
  (v) hinge, CH2 and CH3 regions of human IgG4 containing Ser228Pro and Leu235Ala mutations.

13. The dual-function protein of embodiment 1, wherein the amino acid sequence of said dual-function protein is shown in SEQ ID NO: 13 or 15.

14. A DNA molecule encoding the dual-function protein of any of embodiments 1-13.

15. The DNA molecule of embodiment 14, wherein said DNA molecule comprises the sequence as shown in SEQ ID NO: 14.

16. A vector, wherein the vector comprises the DNA molecule of embodiment 14 or 15.

17. A host cell, wherein the host cell comprises the vector of embodiment 16, or is transfected with the vector comprising the DNA molecule of embodiment 14 or 15.

18. A pharmaceutical composition, wherein the pharmaceutical composition comprises a pharmaceutically acceptable carrier, excipient or diluent, and an effective dose of the dual-function protein of any of embodiments 1-13.

19. A method for preparing the dual-function protein of any of embodiments 1-13, comprising:
  (a) introducing the DNA sequence encoding the dual-function protein of embodiment 14 or 15 into a mammalian cell;
  (b) screening a high-yield cell strain expressing more than 20 pg/$10^6$ (million) cells within a period of every 24 hours in the growth medium thereof from step (a);
  (c) culturing the screened cell strain in step (b), and expressing the dual-function protein;
  (d) harvesting fermentation supernatant obtained from step (c), and purifying the dual-function protein; preferably, said mammalian cell in step (a) is a CHO cell; and more preferably, said mammalian cell is CHO-derived cell line DXB-11.

20. The use of the dual-function protein of any of embodiments 1-13 in the preparation of a drug substance for treating FGF21 related diseases and GLP-1 related diseases, and other metabolic, endocrine and cardiovascular diseases; preferably, said diseases comprise obesity, types 1 and 2 diabetes, pancreatitis, dyslipidemia, nonalcoholic fatty liver disease, nonalcoholic steatohepatitis, insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, nephropathy, diabetic complication, neuropathy, gastroparesis, and symptoms associated with the severe inactivation mutations of insulin receptor; and more preferably, said diseases comprise obesity, types 1 and 2 diabetes, dyslipidemia, nonalcoholic fatty liver disease, nonalcoholic steatohepatitis and metabolic syndrome.

EXAMPLES

Example 1: Construction of an Expression Plasmid of the Synergistic Dual Function Protein All gene sequences encoding alpha 1 microglobulin secretion leader signal, GLP-1 analog, L1, FGF21 mature protein, L2 (comprising a flexible linker unit and rigid linker unit) and human IgG Fc variants were optimized using CHO preferred codons and the full-length gene sequences were synthesized. There are a SpeI at the 5' and a EcoRI at the 3' for subcloning the target gene encoding the fusion protein into the expression vector PXY1A1 modified from PCDNA3.1 (FIG. 1 exemplarily set forth the nucleotide sequence of the dual-function protein FP4I-2 and the translated amino acid sequence). The expression plasmid contained the early promoter of cytomegalovirus, leading to high expression of exogenous genes in mammalian cells. The plasmid also contained a selective marker conferring kanamycin resistance in bacteria, and G418 resistance in mammalian cells. Furthermore, the host cell carrying DHFR-mutant, PXY1A1 expression vector contained the gene of mouse dihydrofolate reductase (DHFR) could amplify the fusion gene and DHFR gene in the absence of methotrexate (MTX) (see U.S. Pat. No. 4,399,216).

Various dual-function proteins comprising GLP-1 and FGF21 were constructed. Here, three are exemplified: FP4I-1, FP4I-2 and FP4I-3. The amino acid composition is shown in Table 1 (L1 and L2 were underlined, and mutated amino acids in Fc variants were boxed).

TABLE 1

Amino acid composition of each synergistic dual function protein

| | |
|---|---|
| FP4I-1 | HGEGTFTSDVSSYLEGQAAKEFIAWLVKGRGGGGSGGGGSGGGGSH PIPDSSPLLQFGGQVRQRYLYTDDAQQTEAHLEIREDGTVGGAADQ SPESLLQLKALKPGVIQILGVKTSRFLCQRPDGALYGSLHFDPEAC SFRELLLEDGYNVYQSEAHGLPLHLPGNKSPHRDPAPRGPARFLPL PGLPPAPPEPPGILAPQPPDVGSSDPLSMVGPSQGRSPSYASGGGG SGGGGSGGGGSGGGGSGGGGSSSSSKAPPPSSSSSKAPPPSESKYG PPCPPCPAPEFAGGPSVFLFPPKPKDTLMISRTPEVTCVVVDVSQ EDPEVQFNWYVDGVEVHNAKTKPREEQFNSTYRVVSVLTVLHQDWL NGKEYKCKVSNKGLPSSIEKTISKAKGQPREPQVYTLPPSQEEMTK NQVSLTCLVKGFYPSDIAVEWESNGQPENNYKTTPPVLDSDGSFFL YSRLTVDKSRWQEGNVFSCSVMHEALHNHYTQKSLSLSLGK<br>(SEQ ID NO: 15) |
| FP4I-2 | HGEGTFTSDVSSYLEEQAAKEFIAWLVKGGGGGGGSGGGGSGGGGS HPIPDSSPLLQFGGQVRQRYLYTDDAQQTEAHLEIREDGTVGGAAD QSPESLLQLKALKPGVIQILGVKTSRFLCQRPDGALYGSLHFDPEA CSFRELLLEDGYNVYQSEAHGLPLHLPGNKSPHRDPAPRGPARFLP LPGLPPAPPEPPGILAPQPPDVGSSDPLSMVGPSQGRSPSYASGSG GGGSGGGGSGGGGSGGGGSGGGGSSSSSKAPPPSLPSPSRLPGPSD TPILPQVECPPCPAPPVAGPSVFLFPPKPKDQLMISRTPEVTCVV VDVSHEDPEVQFNWYVDGVEVHNAKTKPREEQFNSTFRVVSVLTVV HQDWLNGKEYKCKVSNKGLPASIEKTISKTKGQPREPQVYTLPPS REEMTKNQVSLTCLVKGFYPSDIAVEWESNGQPENNYKTTPPMLDS DGSFFLYSKLTVDKSRWQQGNVFSCSVLHEALHNHYTQKSLSLSP GK<br>(SEQ ID NO: 13) |
| FP4I-3 | HGEGTFTSDLSKQMEEEAVRLFIEWLKNGGPSSGAPPPSGGGGGGG SGGGGSGGGGSHPIPDSSPLLQFGGQVRQRYLYTDDAQQTEAHLEI REDGTVGGAADQSPESLLQLKALKPGVIQILGVKTSRFLCQRPDGA LYGSLHFDPEACSFRELLLEDGYNVYQSEAHGLPLHLPGNKSPHRD PAPRGPARFLPLPGLPPAPPEPPGILAPQPPDVGSSDPLSMVGPSQ GRSPSYASGSGGGGSGGGGSGGGGSGGGGSGGGGSSSSSKAPPPSL PSPSRLPGPSDTPILPQVECPPCPAPPVAGPSVFLFPPKPKDQLM ISRTPEVTCVVVDVSHEDPEVQFNWYVDGVEVHNAKTKPREEQFNS TFRVVSVLTVVHQDWLNGKEYKCKVSNKGLPASIEKTISKTKGQP REPQVYTLPPSREEMTKNQVSLTCLVKGFYPSDIAVEWESNGQPEN NYKTTPPMLDSDGSFFLYSKLTVDKSRWQQGNVFSCSVLHEALHNH YTQKSLSLSPGKVDKSRWQQGNVFSCSVLHEALHNHYTQKSLSLS PGK<br>(SEQ ID NO: 32) |

Example 2: Expression of the Dual-Function Protein in a Transfected Cell Line A recombinant expression vector plasmid was transfected into a mammalian host cell line to express the synergistic dual function protein. In order to stabilize the high expression, a preferred host cell line was DHFR defective CHO-cell (U.S. Pat. No. 4,818,679). In the present example, the host cell was selected from CHO-derived cell line DXB11. A preferred transfection method was electroporation, but other methods such as calcium phosphate and liposome-induced transfection also can be used. A Gene Pulser electroporation apparatus (Bio-Rad Laboratories, Hercules, CA) setting at 300 V of electric field and 1500 pFd of capacitance was used in the present experiment and 50 pg pure expression plasmid was mixed with $5 \times 10^7$ CHO cells in the cuvette. Two days after the transfection, a selection medium containing 0.6 mg/mL G418 was used. Quantitative ELISA using anti-human IgG Fc was applied to screen the transfectants with the resistance to G418. Anti-human FGF21 or anti-human GLP-1 by ELISA was used to quantify expression of the dual-function protein. A 96 well culture plate was subjected to the limiting dilution, the well generating a high level of the dual-function protein was subcloned.

In order to achieve a relatively high expression of the dual-function protein, it was appropriate to use the DHFR gene inhibited by MTX for co-amplification. In another selection medium containing incremental concentrations of MTX, the gene of the dual-function protein was co-amplified with the DHFR gene. The subclone with a positive DHFR expression was subjected to the limiting dilution, the selection pressure was gradually increased and the transfectant which can grow in a medium with up to 6 μM MTX was selected. The secreting rate of transfectant was determined and the cell line with a high expression of exogenous protein was screened out. The cell lines with secretory rate higher than about 10 (preferably about 20) $\mu g/10^6$ (i.e. a million) cells/24 hours was subjected to an adaptive suspension culture in serum-free medium, then the dual-function protein was purified by a specified medium.

Example 3: Purification and Qualification of the Dual-Function Protein

This example describes the exemplary purification and qualification methods of FP4I-2. The cell culture supernatant was subjected to clarifying treatments, such as high speed refrigerated centrifugation and 0.22 μm sterile filtration etc., then purified by three chromatograph steps including protein A, anion exchange and hydrophobic chromatography, the specific method was as follows: In the first step, protein A was used for capture, wherein the equilibrium solution was PBS buffer, the eluant was a citrate buffer at pH 3.5, then the eluted protein was neutralized by 1 M Tris solution. In the intermediate purification process, high resolution anion exchange packing material Q Sepharose HP (GE company) was selected to remove residual impurity proteins. A combined mode was used, that is, 20 mM Tris-HCl, 0.2 M NaCl, pH 7.5 solution was used for rinsing, and 20 mM Tris-HCl, 0.3 M NaCl, pH 7.5 solution was used for elution. In the fine purification step, Butyl Sepharose FF (GE) was selected to remove polymers; due to different hydrophobic properties of FP4I-2 monomer and polymer, the monomer with weak hydrophobic property flowed through directly, but the polymer with high hydrophobic property bound to the medium; hydrophobic chromatography was selected as flow through mode, and the equilibrium solution was PBS buffer.

Figure 2B:
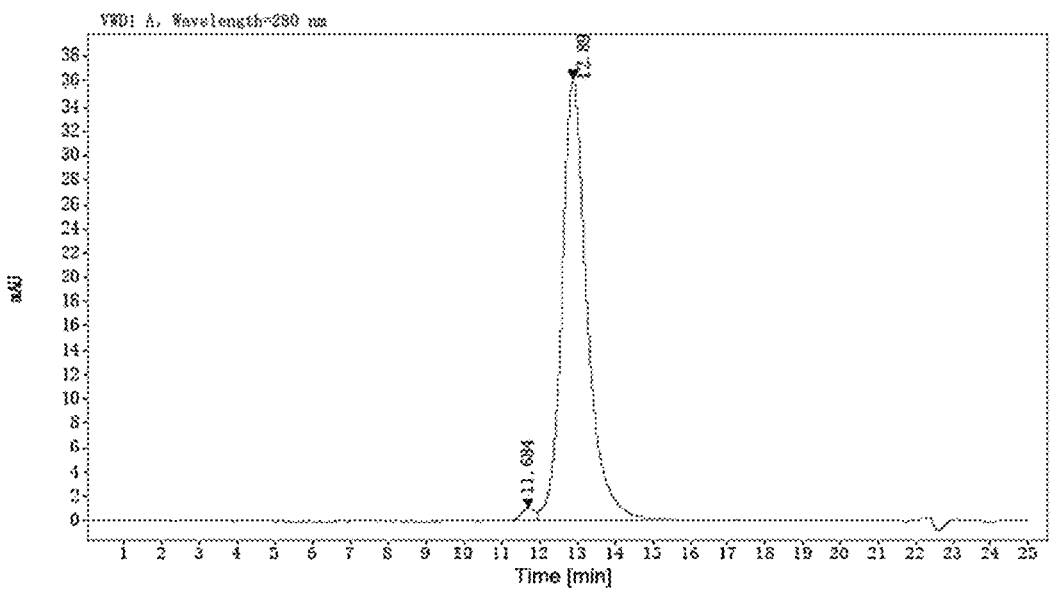
FIG. 2b. SEC-HPLC spectrogram of GLP-1-FGF21 dual-function protein FP4I-2.

The qualitative analysis result is shown in FIGS. 2a and 2b. The theoretical molecular weight of single stranded FP4I-2 was about 53 KD, due to the absence of glycosylation sites, under the reducing condition, SDS-PAGE electrophoresis showed that the actual mass of the single stranded FP4I-2 molecule was about 70 KD. FP4I-1 and -3 were prepared by the same method.

Example 4: Effect of a Single Injection of the Dual-Function Protein on Glucose Utilization in C57BL/6 Mice 8 weeks aged male C57BL/6J mice at SPF grade (purchased from Beijing HFK Bioscience Ltd.) were selected. Housing conditions: temperature 22-25° C., relative humidity 45-65%, and 12h-light/dark cycle. After acclimation for 1 week, mice were randomly divided into control group, Dulaglutide 120 nmol/kg group, FP4I-2 120 nmol/kg group and FP4I-1 120 nmol/kg group (n=7) according to body weight. The mice in the treatment groups were injected subcutaneously with corresponding drug solutions, while the mice in the control group were injected subcutaneously with PBS buffer. After the injection, mice in each group were fasted for 16 h, and then glucose tolerance test was performed. The fasting blood glucose values of the mice were determined followed by an intraperitoneal injection of a 2 g/kg glucose solution, the blood glucose values were determined at 15 min, 30 min, 60 min, 90 min and 120 min after glucose injection, and the increased area below the curve and above the baseline (iAUC) was calculated by the trapezoidal method. The glucose tolerance test was further performed on the mice of each group at 96 h and 144 h after the administration, and the method was the same as above. The data were represented as means±SEM, and analyzed using SPSS18.0 statistical software. For the Gaussian distribution data, statistical comparison of the means among the groups was performed using one-way ANOVA, followed by LSD test for the homogeneity of variance or Dunnet T3 test for the heterogeneity of variance; non-parametric test was used for the Non-Gaussian distribution data. $P<0.05$ represented a significant statistical difference.

Figure 3A:
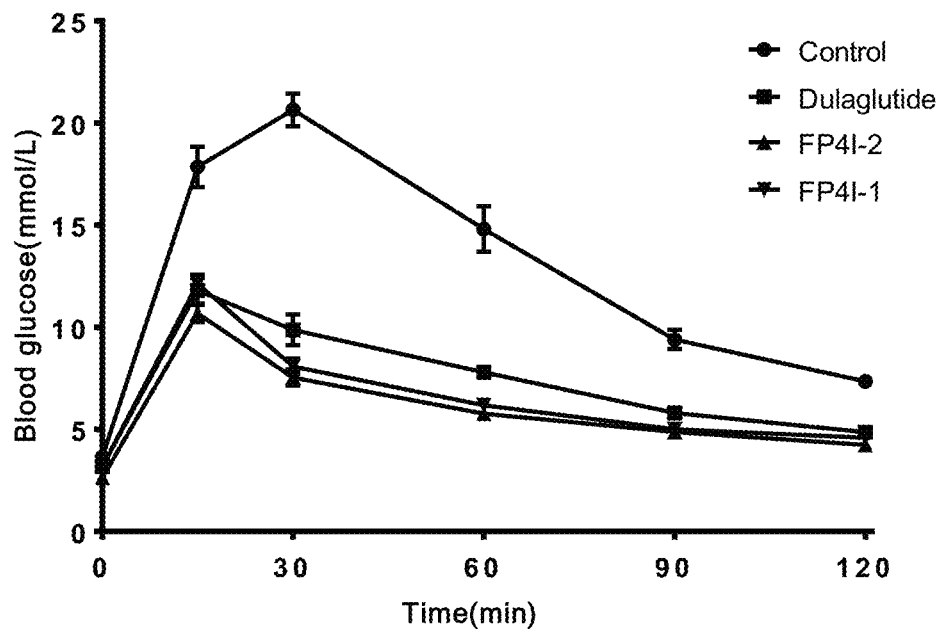
FIG. 3a. Glucose tolerance test curve of GLP-1-FGF21 dual-function proteins FP4I-1 and FP4I-2 16 h after a single injection (means±SEM, n=8).
Figure 3B:
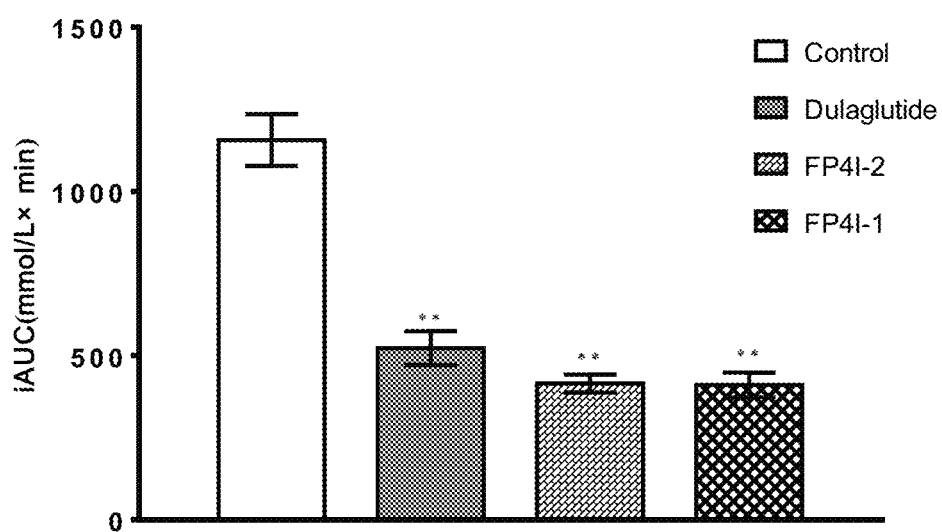
FIG. 3b. Glucose tolerance test iAUC of GLP-1-FGF21 dual-function proteins FP4I-1 and FP4I-2 16 h after a single injection (means±SEM, n=8); statistical difference symbols: compared with the control group, *P<0.05, and **P<0.01.
Figure 4A:
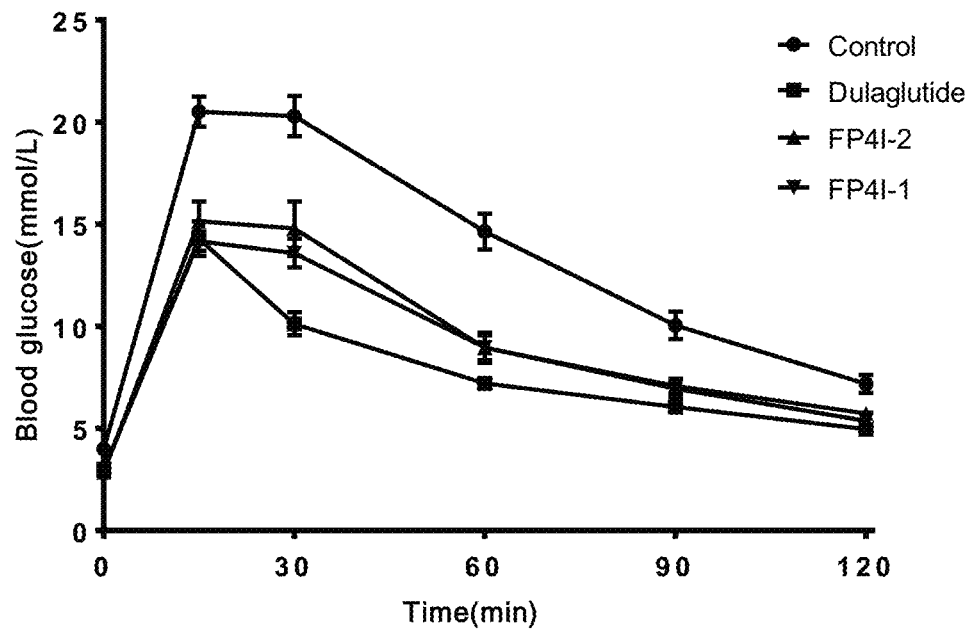
FIG. 4a. Glucose tolerance test curve of GLP-1-FGF21 dual-function proteins FP4I-1 and FP4I-2 96 h after a single injection (means±SEM, n=8).
Figure 4B:
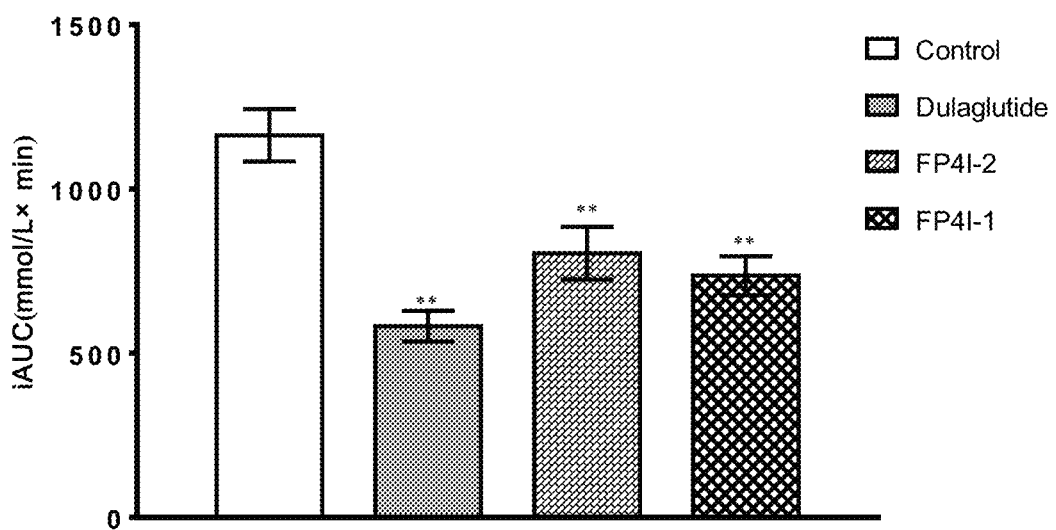
FIG. 4b. Glucose tolerance test iAUC of GLP-1-FGF21 dual-function proteins FP4I-1 and FP4I-2 96 h after a single injection (means±SEM, n=8); statistical difference symbols: compared with the control group, *P<0.05, and **P<0.01.
Figure 5A:
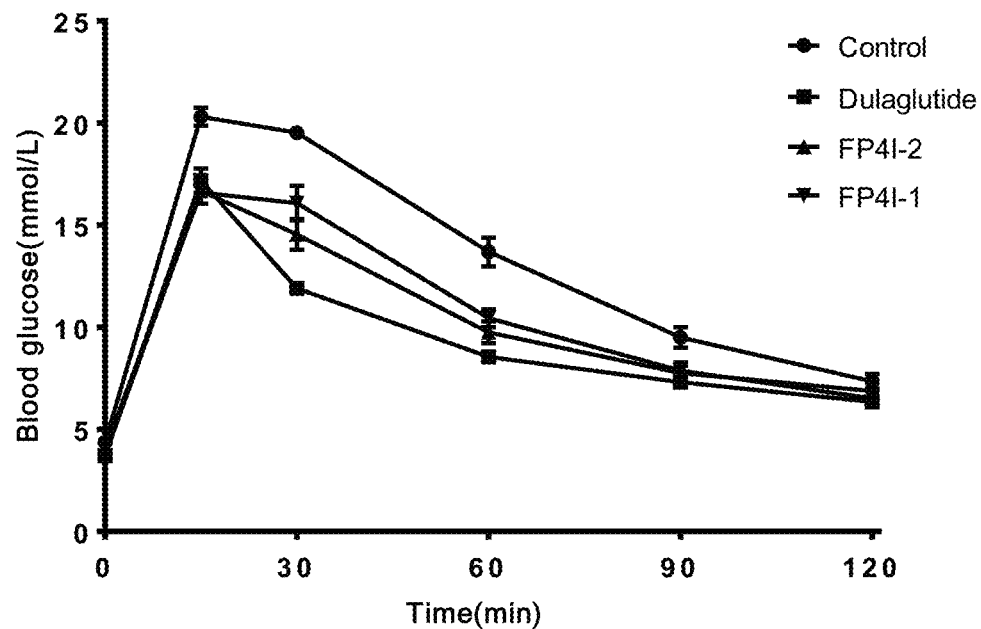
FIG. 5a. Glucose tolerance test curve of GLP-1-FGF21 dual-function proteins FP4I-1 and FP4I-2 144 h after a single injection (means±SEM, n=8).
Figure 5B:
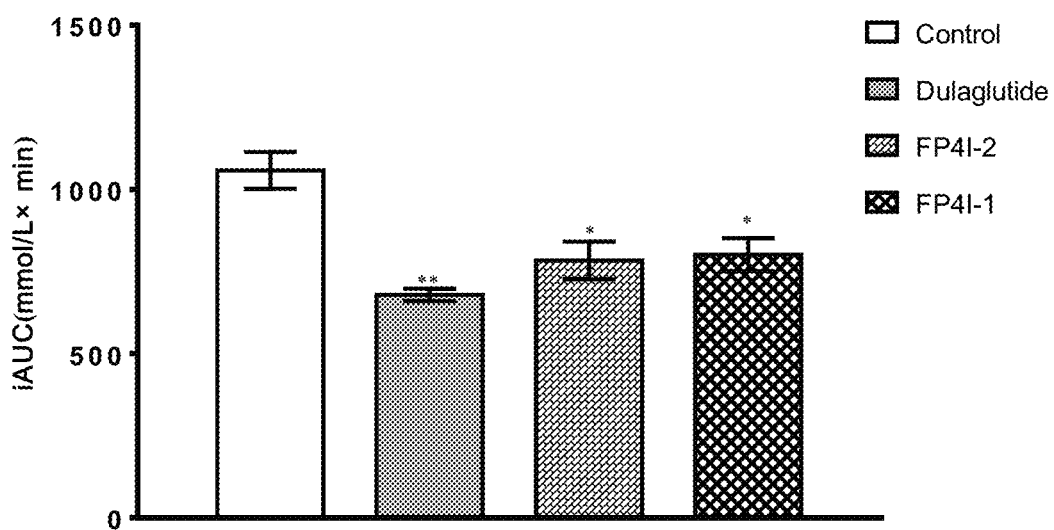
FIG. 5b. Glucose tolerance test iAUC of GLP-1-FGF21 dual-function proteins FP4I-1 and FP4I-2 144 h after a single injection (means±SEM, n=8); statistical difference symbols: compared with the control group, *P<0.05, and **P<0.01.

As shown in FIGS. 3a and 3b, FP4I-1 and FP4I-2 significantly improved glucose utilization in the mice at 16 h after administration when compared with the control group ($P<0.01$). It can be known from FIGS. 4a and 4b that FP4I-1 and FP4I-2 also can significantly improve the glucose utilization level in mice at 96 h after administration as well ($P<0.01$). It can be known from FIGS. 5a and 5b that FP4I-1 and FP4I-2 significantly improved the glucose utilization level in mice even at 144 h after administration ($P<0.05$). The results showed that in the case of a suddenly increased glucose level in vivo, the GLP-1-FGF21 dual-function protein had a rapid response to the glucose level and normalized it to the physiological level by promoting release and secretion of insulin with a long-acting activity, and therefore it could be used for treating diabetes and the complications induced by the absolute or relative deficiency of insulin. When the mice were fasted for 16 h after FP4I-1 or FP4I-2 administration, no shock or death due to hypoglycemia were noted in any mouse, indicating that the dual-function protein would not result in hypoglycemic symptoms as insulin.

Figure 6A:
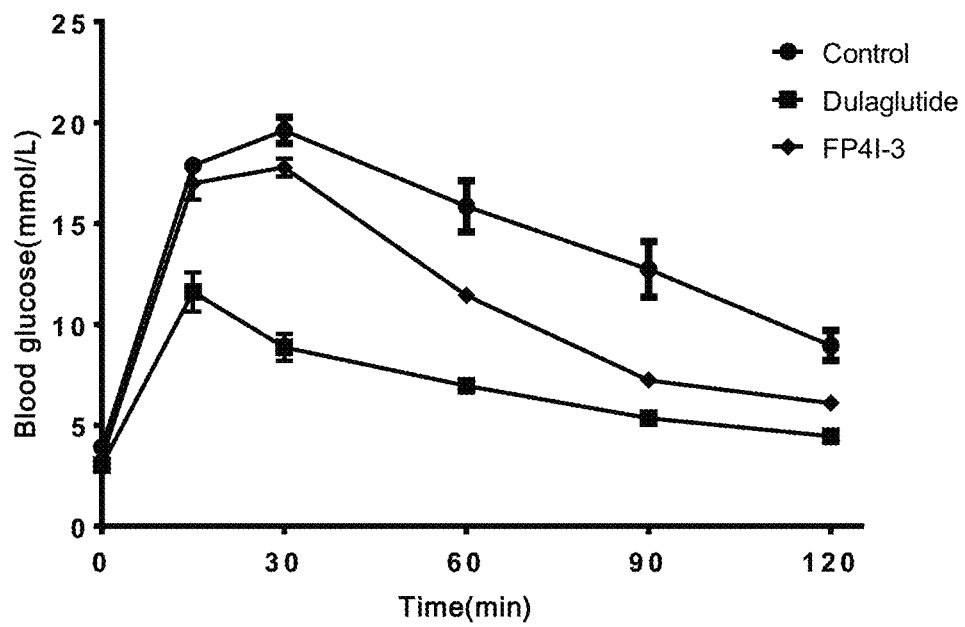
FIG. 6a. Glucose tolerance test curve of Exendin4-FGF21 dual-function proteins FP4I-3 16 h after a single injection (means±SEM, n=8).
Figure 6B:
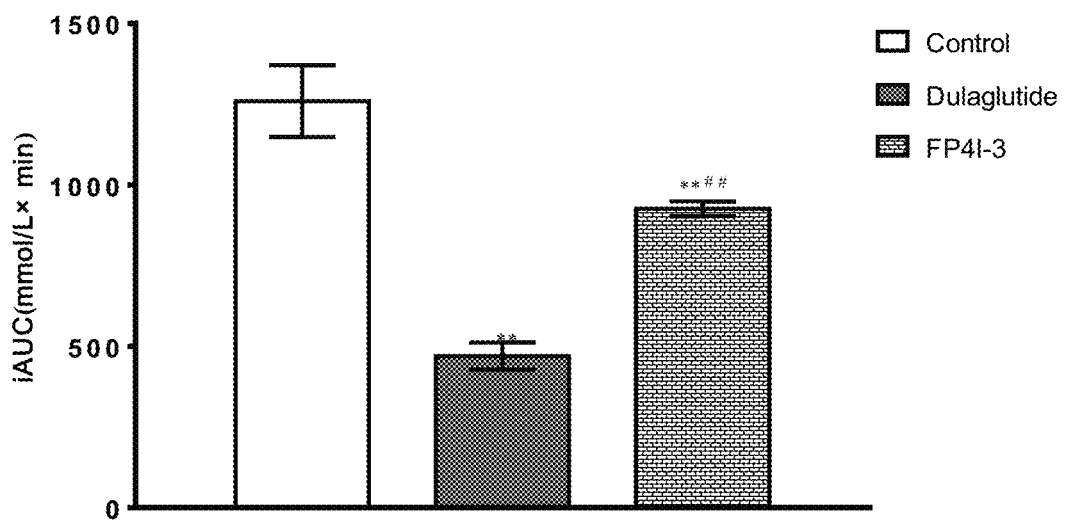
FIG. 6b. Glucose tolerance test iAUC of Exendin4-FGF21 dual-function proteins FP4I-3 16 h after a single injection (means±SEM, n=8); statistical difference symbols: compared with the control group, *P<0.05, and **P<0.01; compared with the Dulaglutide group, #P<0.05, and ##P<0.01.
Figure 7A:
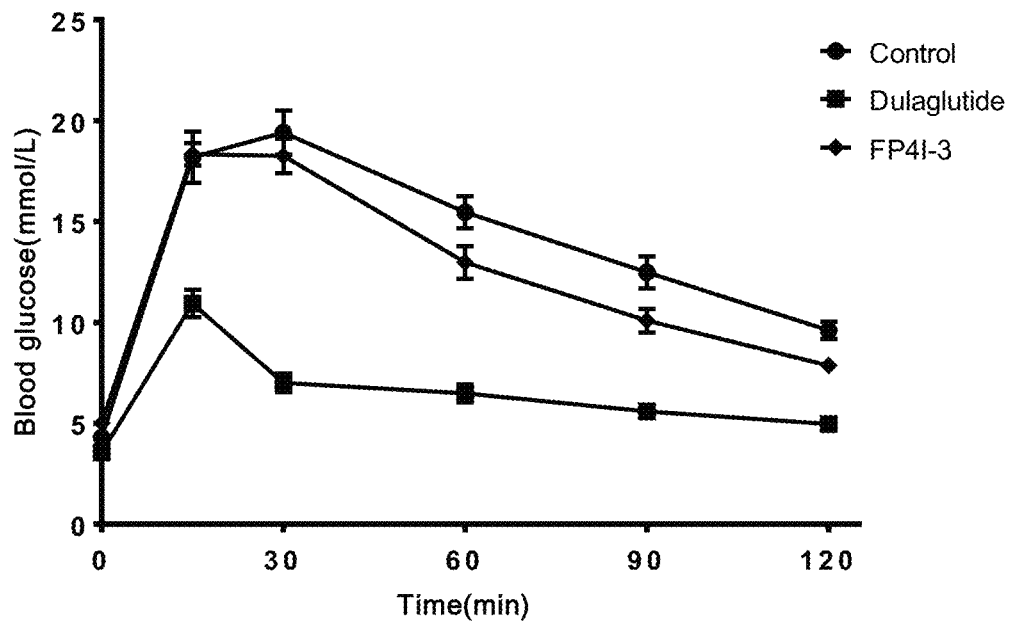
FIG. 7a. Glucose tolerance test curve of Exendin4-FGF21 dual-function proteins FP4I-3 96 h after a single injection (means±SEM, n=8).
Figure 7B:
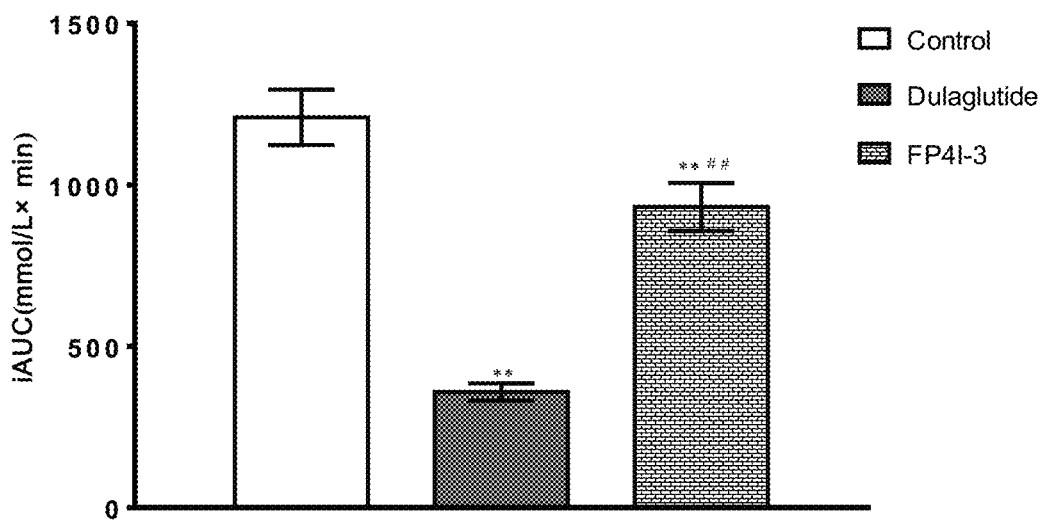
FIG. 7b. Glucose tolerance test iAUC of Exendin4-FGF21 dual-function proteins FP4I-3 96 h after a single injection (means±SEM, n=8); statistical difference symbols: compared with the control group, *P<0.05, and **P<0.01; compared with the Dulaglutide group, #P<0.05, and ##P<0.01.
Figure 8A:
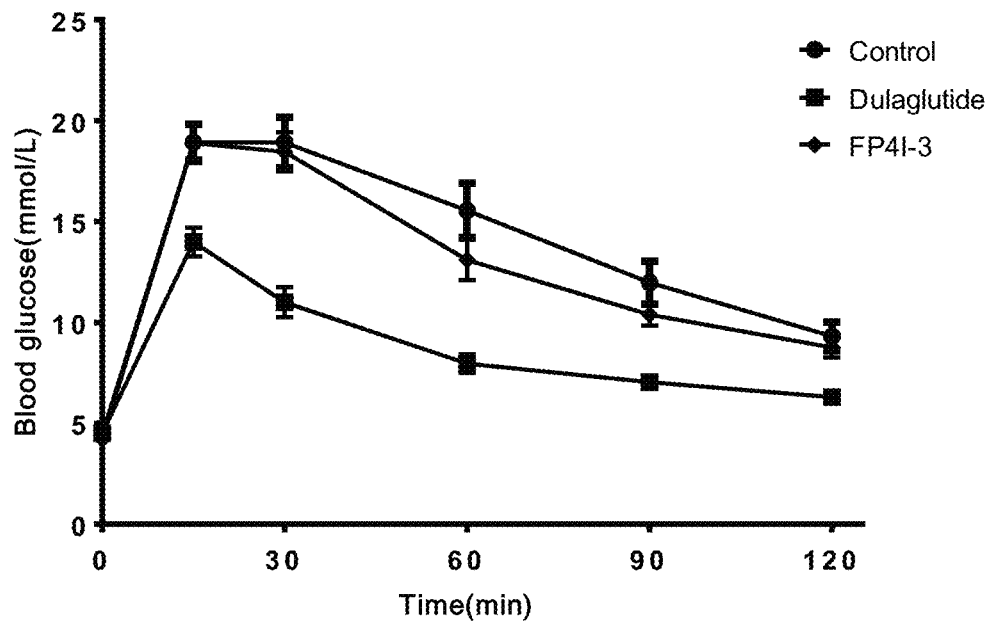
FIG. 8a. Glucose tolerance test curve of Exendin4-FGF21 dual-function proteins FP4I-3 144 h after a single injection (means±SEM, n=8).
Figure 8B:
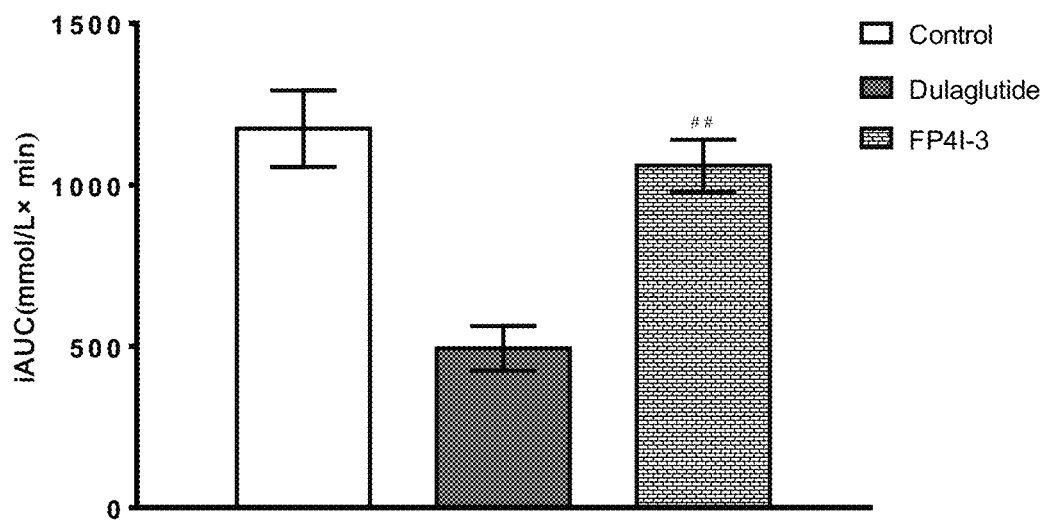
FIG. 8b. Glucose tolerance test iAUC of Exendin4-FGF21 dual-function proteins FP4I-3 144 h after a single injection (means±SEM, n=8); statistical difference symbols: compared with the control group, *P<0.05, and **P<0.01; compared with the Dulaglutide group, #P<0.05, and ##P<0.01.
Figure 16:
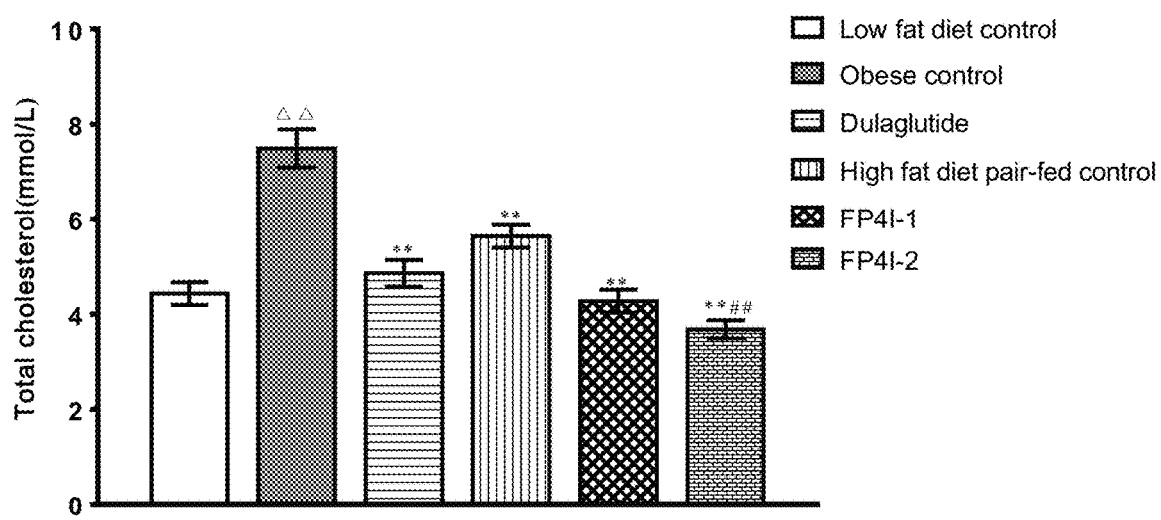
FIG. 16. Effect of GLP-1-FGF21 dual-function proteins FP4I-1 and FP4I-2 on serum total cholesterol content in obese mice induced by high-fat diet (means±SEM, n=7); statistical difference symbols: compared with the obesity control group, *P<0.05, and **P<0.01; compared with the Dulaglutide group, #P<0.05, and ##P<0.01.
Figure 17:
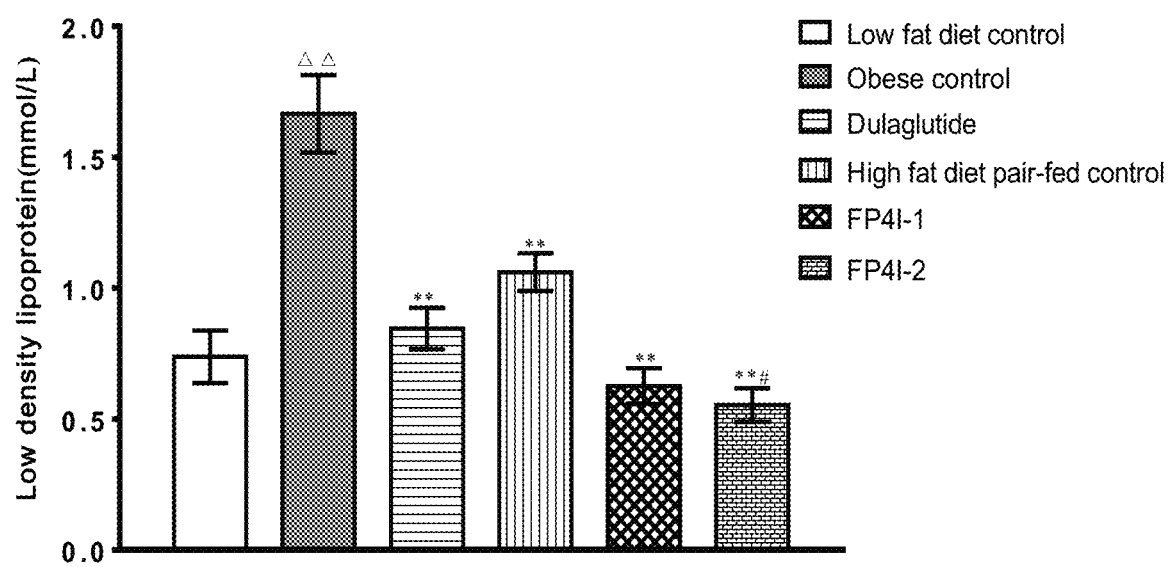
FIG. 17. Effect of GLP-1-FGF21 dual-function proteins FP4I-1 and FP4I-2 on serum low density lipoprotein cholesterol content in obese mice induced by high-fat diet (means±SEM, n=7); statistical difference symbols: compared with the obesity control group, *P<0.05, and **P<0.01; compared with the Dulaglutide group, #P<0.05, and ##P <0.01.

In addition, the activity of Exendin4-FGF21 dual-function protein FP4I-3 on the glucose utilization was determined by above-mentioned method as well. C57BL/6 mice were divided into the control group, Dulaglutide group and FP4I-3 group. Corresponding drug solutions (120 nmol/kg) were administrated subcutaneously to the mice in Dulaglutide group and FP4I-3 group, respectively, and PBS buffer was administrated to the mice in the control group. The glucose tolerance test was performed at 16 h, 96 h, and 144 h after the injection. As shown in FIGS. 6a and 6b, 16 h after the administration, compared with the control group, FP4I-3 significantly improved the glucose utilization ($P<0.01$), but the activity was significantly weaker than that of Dulaglutide ($P<0.01$). As shown in FIGS. 7a and 7b, 96 h after the administration, FP4I-3 significantly improved the glucose utilization in mice ($P<0.01$) though the efficacy was significantly lower than Dulaglutide as well ($P<0.01$). As shown in FIGS. 8a and 8b, 144 h after the administration, the ability of FP4I-3 to improve glucose utilization in mice was not observed ($P>0.05$).

The glucose tolerance test of FP4I-3 in animals demonstrated that Exendin-4 did not display a synergistic effect with FGF21. The hypoglycemic effect of FP4I-3 was significantly weaker than that of Dulaglutide indicated that the circulating half-life of FP4I-3 was shorter than Dulaglutide. In contrast, the preferred GLP-1-FGF21 dual-function proteins FP4I-2 and FP4I-1 had a relatively strong stability in vivo, and were not easily degraded and inactivated, and maintained a longer in vivo pharmacodynamic activity relative to Exendin4-FGF21 dual-function protein FP4I-3. Above results indicated that the combination modes of three functional components, GLP-1 analogs, FGF21 and Fc fragment in the dual-function protein were not random and arbitrarily, wherein the selection of GLP-1 analogs, the structure of linker peptide, the fusion sequence, even the difference of glycosylation pattern would affect accuracy and stability of the dual-function protein conformation to varying degrees, and it determined whether the active molecules were functionally synergetic and the half-life was prolonged or not.

Example 5: Hypoglycemic Effect of Dual-Function Protein in db/db Mice 8 weeks aged male db/db mice were purchased from Shanghai SLAC Laboratory Animal Ltd. Housing conditions: temperature 22-25° C., relative humidity 45-65%, and 12 h-light/dark cycle. After housed individually for 1 week as acclimation, the mice were divided into 4 groups according to body weight, blood glucose and food intake: control group, Dulaglutide group, FP4I-1 group and FP4I-2 group (n=7). Mice in the control group were injected subcutaneously with PBS buffer, and mice in other groups were injected subcutaneously with 120 nmol/kg corresponding drug solutions (twice per week, totally 8 times). Daily food intake of each mouse was recorded. At the end of the dosing period, mice were fasted for 16 hours, 5 µL whole blood sample was collected from the eye socket to measure glycosylated hemoglobin. The data were represented as means±standard error ($\bar{x}±s$), and were analyzed using SPSS 18.0 statistical software. For the data follow Gaussian distribution, one-way analysis of variance was used for comparing mean difference among groups, followed by LSD test for the homogeneity of variance or Dunnet T3 test for the heterogeneity of variance; non-parametric test was used for the data follow non-normal distribution. $P<0.05$ represented a significant statistical difference.

Figure 9:
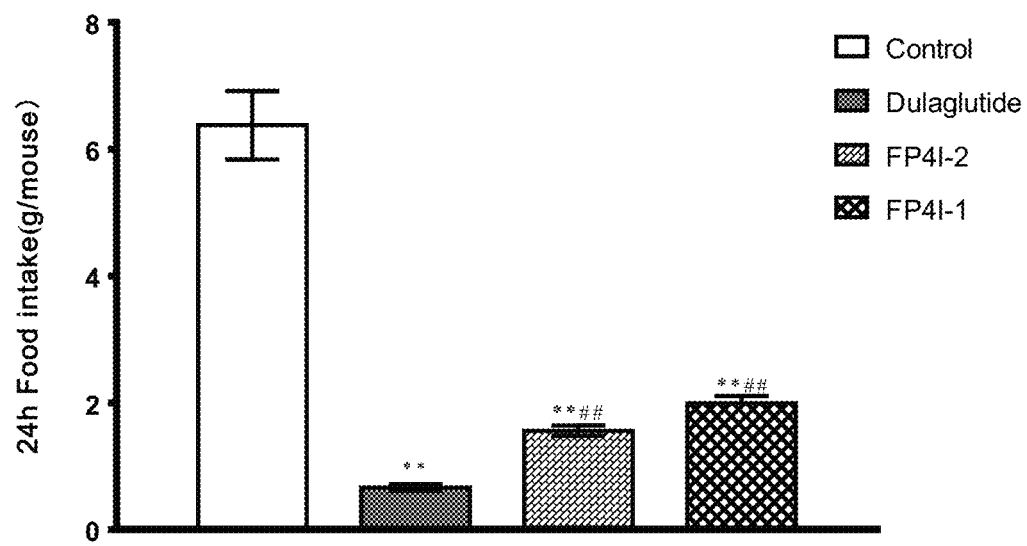
FIG. 9. Effect of GLP-1-FGF21 dual-function proteins FP4I-1 and FP4I-2 on 24 h food intake in db/db mice after first administration (means±SEM, n=6); statistical difference symbols: compared with the control group, *P<0.05, and **P<0.01; compared with the Dulaglutide group, #P<0.05, and ##P<0.01.
Figure 10:
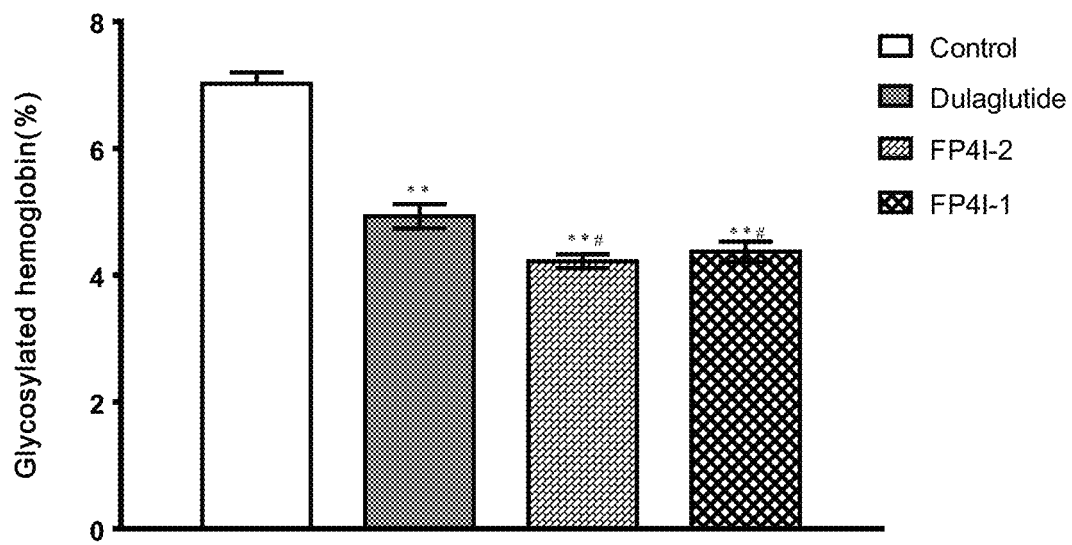
FIG. 10. Effect of multiple administrations of GLP-1-FGF21 dual-function proteins FP4I-1 and FP4I-2 on glycated hemoglobin in db/db mice (means±SEM, n=6); statistical difference symbols: compared with the control group, *P<0.05, and **P<0.01; compared with the Dulaglutide group, #P<0.05, and ##P<0.01.
Figure 11:
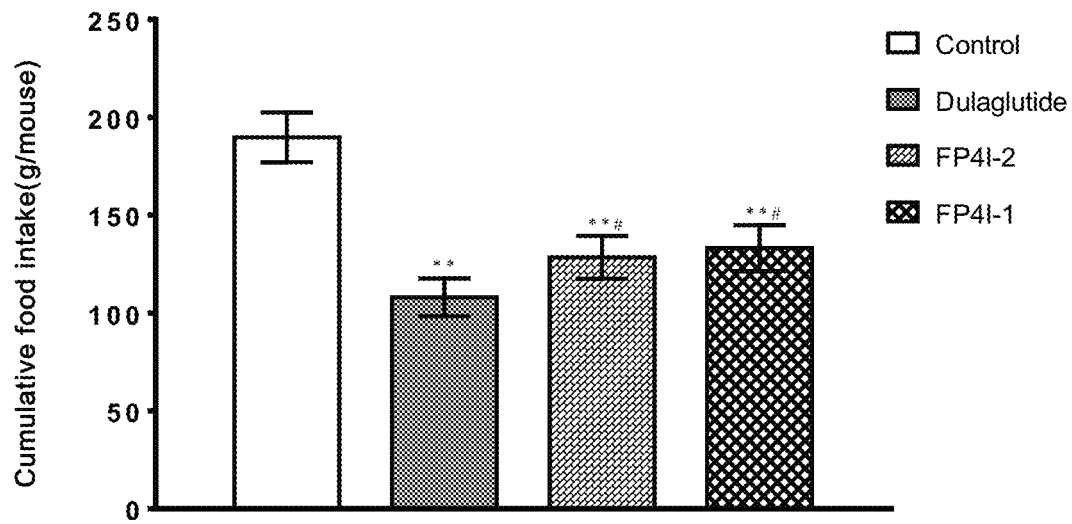
FIG. 11. Effect of multiple administrations of GLP-1-FGF21 dual-function proteins FP4I-1 and FP4I-2 on accumulative food intake in db/db mice (means±SEM, n=6); statistical difference symbols: compared with the control group, *P<0.05, and **P<0.01; compared with the Dulaglutide group, #P<0.05, and OP<0.01.
Figure 12:
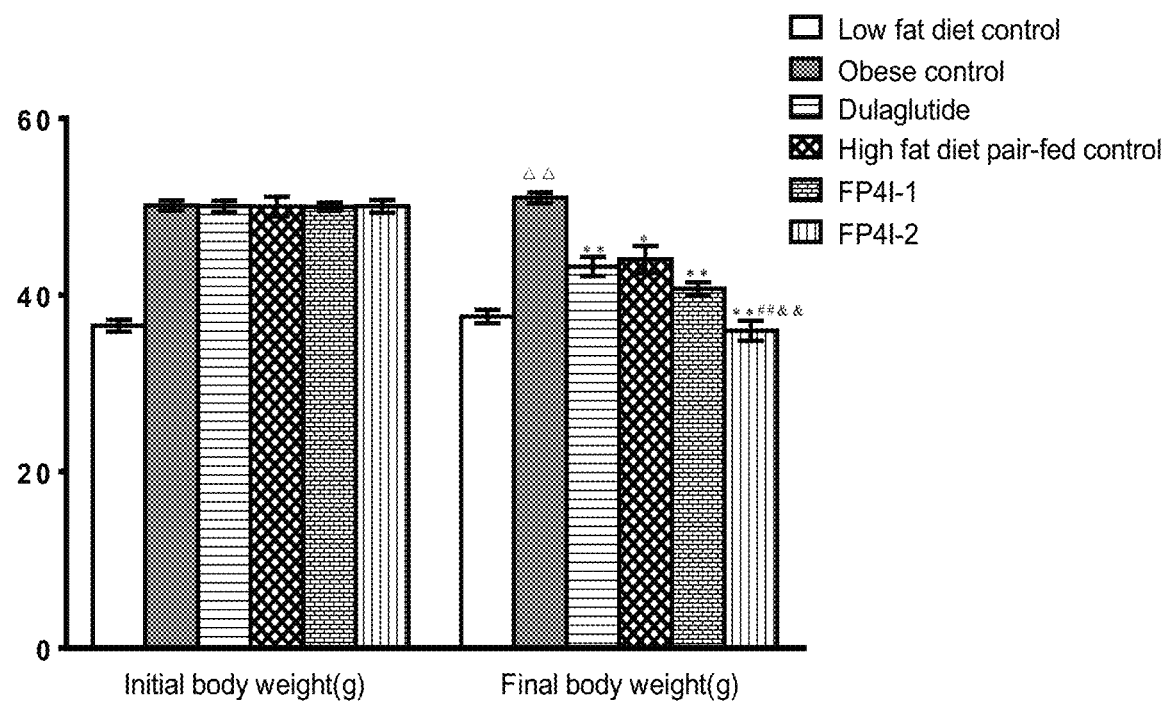
FIG. 12. Effect of GLP-1-FGF21 dual-function proteins FP4I-1 and FP4I-2 on body weight in obese mice induced by high-fat diet (means±SEM, n=7); statistical difference symbols: compared with the obesity control group, *P<0.05, and **P<0.01; compared with the Dulaglutide group, #P<0.05, and ##P<0.01; compared with the FP4I-1 group, &P<0.05, and &&P<0.01.
Figure 13:
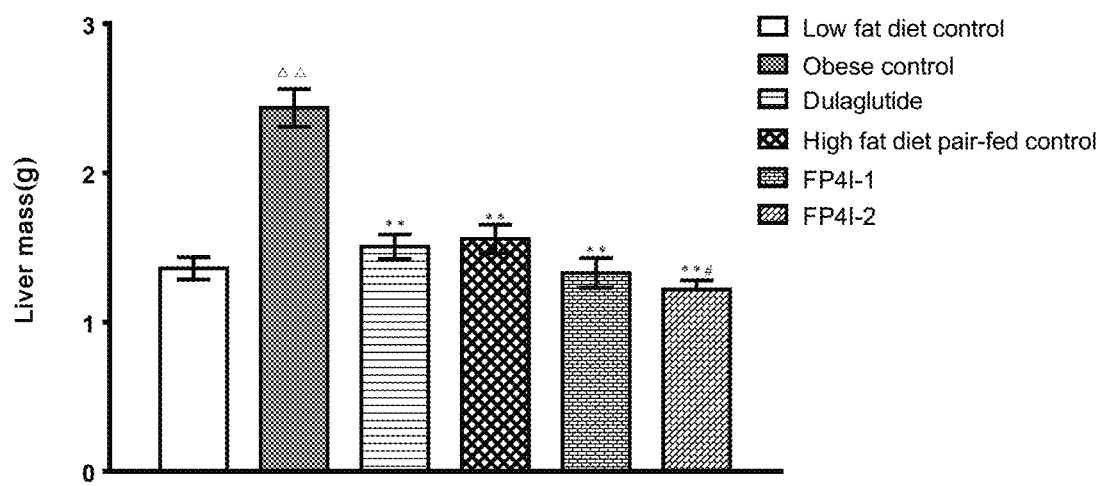
FIG. 13. Effect of GLP-1-FGF21 dual-function proteins FP4I-1 and FP4I-2 on liver mass in obese mice induced by high-fat diet (means±SEM, n=7); statistical difference symbols: compared with the obesity control group, *P<0.05, and **P<0.01; compared with the Dulaglutide group, #P<0.05, and ##P<0.01.
Figure 14:
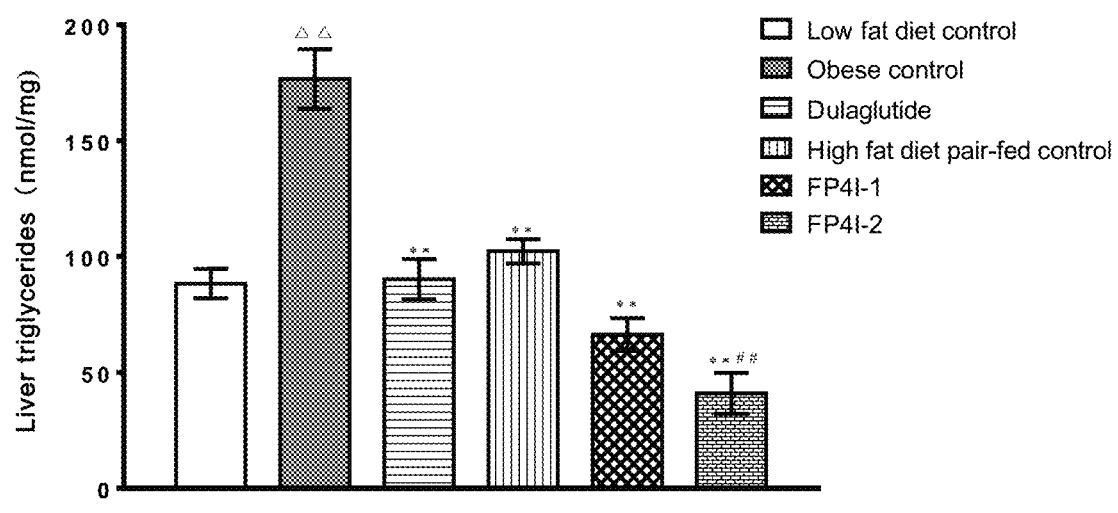
FIG. 14. Effect of GLP-1-FGF21 dual-function proteins FP4I-1 and FP4I-2 on liver triglyceride content in obese mice induced by high-fat diet (means±SEM, n=7); statistical difference symbols: compared with the obesity control group, *P<0.05, and **P <0.01; compared with the Dulaglutide group, #P<0.05, and ##P<0.01.
Figure 15:
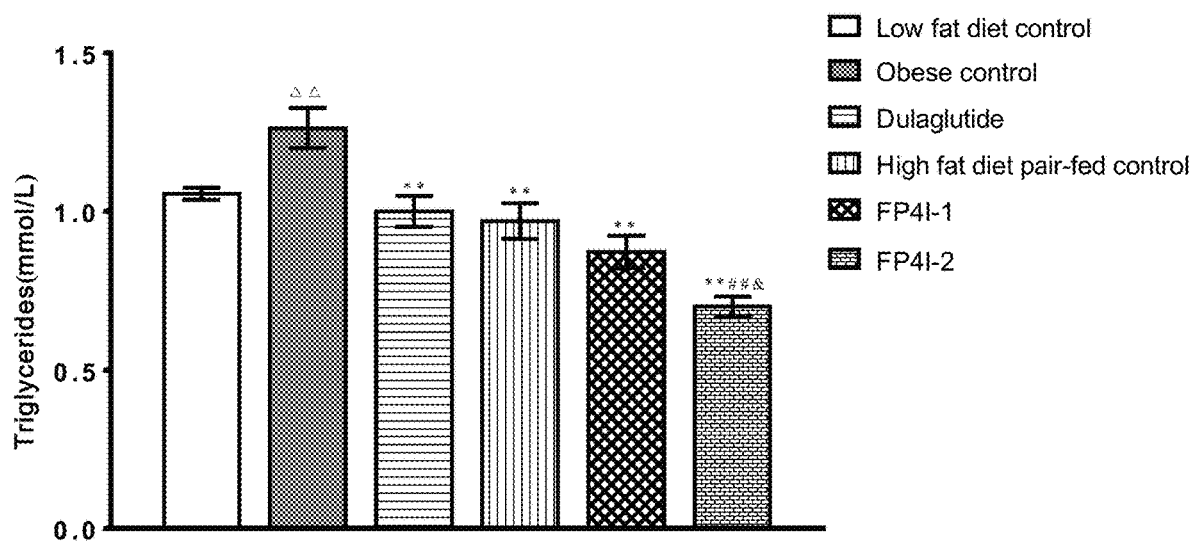
FIG. 15. Effect of GLP-1-FGF21 dual-function proteins FP4I-1 and FP4I-2 on serum triglyceride in obese mice induced by high-fat diet (means±SEM, n=7); statistical difference symbols: compared with the obesity control group, *P<0.05, and **P<0.01; compared with the Dulaglutide group, #P<0.05, and ##P<0.01; compared with the FP4I-1 group, &P<0.05, and &&P<0.01.

As shown in FIG. 9, compared with Dulaglutide group, after the first administration, the food intakes within 24 hour of the mice in FP4I-1 and FP4I-2 groups were significantly elevated ($P<0.01$). The results showed that GLP-1-FGF21 dual-function protein could significantly relieve symptoms of severe gastrointestinal adverse effects induced by the first administration of long-acting GLP-1 receptor agonist drugs. As shown in FIG. 10, FP4I-1, FP4I-2, Dulaglutide group can significantly lower the glycosylated hemoglobin values of db/db mice ($P<0.01$), and the glycosylated hemoglobin values of mice in FP4I-1 and FP4I-2 groups were significantly lower than that in Dulaglutide group ($P<0.05$). db/db mouse is a spontaneously hyperglycemic animal model with a severe insulin tolerance. The GLP-1-FGF21 dual-function protein exhibited a better property than Dulaglutide in the long-term glycemic control. Based on the data in Example 4, the insulinotropic activity of GLP-1-FGF21 dual-function protein was not significantly better than Dulaglutide. Wild type FGF21 exhibited a good insulin sensitization effect in the hypeinsulinemic-euglycemic clamp test (Xu J et al., Diabetes, 2009, 58:250-259), but there was no direct evidence showing that Dulaglutide had an insulin sensitization effect in vivo. In conclusion, the superiority in blood glucose control exhibited by GLP-1-FGF21 dual-function protein should be the result of synergistic effect of GLP-1 analog promoting release and secretion of insulin and FGF21 enhancing insulin sensitivity. As shown in FIG. 11, in the experimental period, the cumulative food intake of mice in FP4I-1 and FP4I-2 groups was significantly higher than that in Dulaglutide group ($P<0.05$), the results showed that in the condition of excluding factors intervening food intake, the blood glucose control activity of FP4I-1 and FP4I-2 groups on type 2 diabetes should be higher than that of Dulaglutide.

Example 6. Therapeutic Effects of the Dual-Function Protein on Weight Loss, Hepatic Steatosis and Lipid Metabolism Disorder in Obese Mice Induced by High-Fat Diet 8 weeks aged C57BL/6 mice were purchased from Shanghai SLAC Laboratory Animal Ltd. Housing conditions: temperature 22-25° C., relative humidity 45-65%, and lighting time 12 h/d. After acclimation for 1 week, 7 mice were selected and fed with low-fat diet (D12450B, Research Diets), and other mice were fed with high-fat diet (D12451, Research Diets). 40 weeks later, obese mice were subjected to adaptive feeding with single animal/cage for 1 week, then the obese mice were divided into five groups according to body weight and weekly food intake: obese control group, Dulaglutide group, high fat diet pair-fed group, FP4I-1 group and FP4I-2 group (n=7). In the experiment, the amounts of daily diet per mouse in high fat diet pair-fed, FP4I-1and FP4I-2 groups were consistent with daily food intake per mouse in Dulaglutide group. Mice in the obese control group and high fat diet pair-fed group were injected subcutaneously with PBS buffer solution, and mice in other groups were injected subcutaneously with 120 nmol/kg corresponding drug solutions, once every 6 days, and totally 2 times. The body weight of each mouse was recorded before and after the dosing period. At the end of the dosing period, mice in each group were fasted for 16 hours, whole blood was collected from the eye socket, and centrifuged at 2000×g for 15 min to obtain serum. Serum lipid profiles were determined by an automatic biochemical analyzer. Liver tissue was excised, washed with normal saline, then removed residual liquid with filter paper and weighed. About 50 mg liver tissue at the same part of each live was taken, and the triglyceride content was determined using the Folch method. The results were represented in the form of triglyceride content per mg liver tissue. The data were represented as means±SEM, and analyzed using SPSS18.0 statistical software. For the Gaussian distribution data, statistical comparison of the means among the groups was performed using one-way ANOVA, followed by LSD test for the homogeneity of variance or Dunnet T3 test for the heterogeneity of variance; non-parametric test was used for the Non-Gaussian distribution data. $P<0.05$ represented a significant statistical difference.

As shown in FIGS. 12 to 17, after administrated with Dulaglutide, body weight, liver mass, liver triglyceride, triglycerides, total cholesterol and low density lipoprotein-cholesterol contents in serum were significantly lowered ($P<0.01$) in the obese mice induced by high-fat diet. Dulaglutide could cause severe gastrointestinal adverse effects and suppressed appetite by regulating central nervous system, resulted in reduction in food intake. In this example, daily supplied the same amount of diet to the mice in the high-fat diet pair-fed group as the corresponding mice in Dulaglutide group, despite the parameters mentioned above were significantly lowered when compared with that in the obese control group, there was no significant statistical difference from that of Dulaglutide group ($P>0.05$). The results showed that the effects of Dulaglutide on weight loss, hepatic steatosis and lipid metabolic disorder substantially depended on inhibition of appetite without any other mechanisms. The obese mice in FP4I-1 group and FP4I-2 group were given the same amount of diet as the corresponding mice in Dulaglutide group, compared with Dulaglutide group, body weight and serum triglyceride level of the mice in FP4I-2 group were significantly decreased ($P<0.01$), which demonstrated that FP4I-2 had additional functions of reducing fatty acid synthesis and promoting fatty acid metabolism and utilization in vivo. The results indicated that FP4I-2 could be used for treating obesity and obesity-induced metabolic syndrome.

Compared with Dulaglutide group, liver mass and liver triglyceride content of mice in FP4I-2 group were significantly decreased ($P<0.01$ or $P<0.05$), which demonstrated that FP4I-2 effectively reduced the excessive accumulation of triglyceride in liver, improved liver function. The results indicated that FP4I-2 could be used for treating various liver diseases induced by hepatic steatosis, such as nonalcoholic fatty liver, nonalcoholic steatohepatitis, liver fibrosis and liver cirrhosis.

Compared with Dulaglutide group, both total serum cholesterol and low density lipoprotein-cholesterol content of mice in FP4I-2 group were significantly reduced ($P<0.01$ or $P<0.05$), indicating that FP4I-2 can be used for treating hypercholesteremia and relevant cardiovascular and cerebrovascular diseases, such as hypertension, coronary heart disease, chronic heart failure, cerebral infarction and atherosclerosis. Compared with Dulaglutide group, the body weight, liver mass, liver triglyceride content, serum triglycerides, total cholesterol and low density lipoprotein cholesterol levels in FP4I-1 group were mildly decreased but no significant differences were observed.

The present study demonstrated that FP4I-1 and FP4I-2 could treat obesity, fatty liver disease and lipid metabolic disorder via the physiological activity of FGF21, and was not completely dependent on the food intake regulation effect of GLP-1 analogs; the therapeutic effect of FP4I-2 in the obese mice was superior to Dulaglutide, which indicated that it could compensate for the deficiency of Dulaglutide in the clinic. In conclusion, the therapeutic mechanisms of FP4I-2 are more abundant than that of Dulaglutide, which is more suitable for the requirement of diversified clinical therapy.

This disclosure provides merely exemplary embodiments of the disclosure. One skilled in the art will readily recognize from the disclosure and claims, that various changes, modifications and variations can be made therein without departing from the spirit and scope of the disclosure as defined in the following claims.

All documents mentioned in this application are hereby incorporated by reference as if each document were individually incorporated by reference. In addition, it should be understood that after reading the above teachings of the invention, those skilled in the art can make various changes or modifications to the invention, and these equivalent forms also fall within the scope defined by the appended claims of this application.

The invention claimed is:

1. A dual-function protein, wherein the amino acid sequence of said dual-function protein comprises SEQ ID NO: 13.

2. A pharmaceutical composition, wherein the pharmaceutical composition comprises a pharmaceutically acceptable carrier, excipient or diluent, and an effective dose of the dual-function protein of claim 1.

3. A method of treatment of one or more diseases selected from type 2 diabetes, glucose intolerance, and hyperglycemia, comprising administering to a person suffering from at least one of said diseases an effective amount of the pharmaceutical composition of claim 2.

4. A method of treatment of one or more diseases selected from type 2 diabetes, glucose intolerance, and hyperglycemia, comprising administering to a person suffering from at least one of said diseases an effective amount of the dual-function protein of claim 1.

5. A dual-function protein, wherein the amino acid sequence of said dual-function protein comprises SEQ ID NO: 15.

6. A pharmaceutical composition, wherein the pharmaceutical composition comprises a pharmaceutically acceptable carrier, excipient or diluent, and an effective dose of the dual-function protein of claim 5.

7. A method of treatment of one or more diseases selected from type 2 diabetes, glucose intolerance, and hyperglycemia, comprising administering to a person suffering from at least one of said diseases an effective amount of the pharmaceutical composition of claim 6.

8. A method of treatment of one or more diseases selected from type 2 diabetes, glucose intolerance, and hyperglycemia, comprising administering to a person suffering from at least one of said diseases an effective amount of the dual-function protein of claim 5.

* * * * *

SEQUENCE LISTING

```
<160> NUMBER OF SEQ ID NOS: 38

<210> SEQ ID NO 1
<211> LENGTH: 31
<212> TYPE: PRT
<213> ORGANISM: Homo sapiens
<220> FEATURE:
<223> OTHER INFORMATION: Amino acid sequence of wild-type human GLP-1

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: Amino acid sequence of GLP-1 analogue 1

<400> SEQUENCE: 2

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys
            20                  25

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of GLP-1 analogue 2

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 4
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of GLP-1 analogue 3

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of GLP-1 analogue 4

<400> SEQUENCE: 5

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 6
<211> LENGTH: 209
<212> TYPE: PRT
<213> ORGANISM: Homo sapiens
<220> FEATURE:
<223> OTHER INFORMATION: Amino acid sequence of wild-type human FGF21

<400> SEQUENCE: 6

```
Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Ala Ala Asp Gln Ser Pro Glu Ser Leu
65              70                  75                  80

Leu Gln Leu Lys Ala Leu Lys Pro Gly Val Ile Gln Ile Leu Gly Val
            85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
            165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of hCG beta-subunits
      (113-145)

<400> SEQUENCE: 7

Pro Arg Phe Gln Asp Ser Ser Ser Ser Lys Ala Pro Pro Ser Leu
1               5                   10                  15

Pro Ser Pro Ser Arg Leu Pro Gly Pro Ser Asp Thr Pro Ile Leu Pro
            20                  25                  30

Gln

<210> SEQ ID NO 8
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of vFc gamma 1

<400> SEQUENCE: 8

Asp Lys Thr His Thr Cys Pro Pro Cys Pro Ala Pro Glu Val Ala Gly
1               5                   10                  15
```

```
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 9
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of vFc gamma 2-1

<400> SEQUENCE: 9

Val Glu Cys Pro Pro Cys Pro Ala Pro Val Ala Gly Pro Ser Val
1                5                  10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
 50                  55                  60

Thr Lys Pro Arg Glu Glu Gln Phe Asn Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
            115                 120                 125
```

```
Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 10
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of vFc gamma 2-2

<400> SEQUENCE: 10

Val Glu Cys Pro Pro Cys Pro Ala Pro Val Ala Gly Pro Ser Val
1               5                   10                  15

Phe Leu Phe Pro Pro Lys Pro Lys Asp Gln Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205

His Asn His Tyr Thr Gln Lys Ser Leu Ser Leu Ser Pro Gly Lys
    210                 215                 220

<210> SEQ ID NO 11
<211> LENGTH: 223
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Amino acid sequence of vFc gamma 2-3

<400> SEQUENCE: 11

Val Glu Cys Pro Pro Cys Pro Ala Pro Pro Val Ala Gly Pro Ser Val
1               5                   10                  15

Phe Leu Phe Pro Pro Lys Pro Lys Asp Gln Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Leu His Glu Ala Leu
        195                 200                 205

His Asn His Tyr Thr Gln Lys Ser Leu Ser Leu Ser Pro Gly Lys
    210                 215                 220

<210> SEQ ID NO 12
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of vFc gamma 4

<400> SEQUENCE: 12

Glu Ser Lys Tyr Gly Pro Pro Cys Pro Pro Cys Pro Ala Pro Glu Phe
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
```

```
                    85                  90                  95
Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 13
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of FP4I-2

<400> SEQUENCE: 13

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Gly Ser His Pro
        35                  40                  45

Ile Pro Asp Ser Ser Pro Leu Leu Gln Phe Gly Gly Gln Val Arg Gln
    50                  55                  60

Arg Tyr Leu Tyr Thr Asp Asp Ala Gln Gln Thr Glu Ala His Leu Glu
65                  70                  75                  80

Ile Arg Glu Asp Gly Thr Val Gly Gly Ala Ala Asp Gln Ser Pro Glu
                85                  90                  95

Ser Leu Leu Gln Leu Lys Ala Leu Lys Pro Gly Val Ile Gln Ile Leu
            100                 105                 110

Gly Val Lys Thr Ser Arg Phe Leu Cys Gln Arg Pro Asp Gly Ala Leu
        115                 120                 125

Tyr Gly Ser Leu His Phe Asp Pro Glu Ala Cys Ser Phe Arg Glu Leu
    130                 135                 140

Leu Leu Glu Asp Gly Tyr Asn Val Tyr Gln Ser Glu Ala His Gly Leu
145                 150                 155                 160

Pro Leu His Leu Pro Gly Asn Lys Ser Pro His Arg Asp Pro Ala Pro
                165                 170                 175

Arg Gly Pro Ala Arg Phe Leu Pro Leu Pro Gly Leu Pro Pro Ala Pro
            180                 185                 190

Pro Glu Pro Pro Gly Ile Leu Ala Pro Gln Pro Pro Asp Val Gly Ser
```

```
                195                 200                 205
Ser Asp Pro Leu Ser Met Val Gly Pro Ser Gln Gly Arg Ser Pro Ser
    210                 215                 220
Tyr Ala Ser Gly Ser Gly Gly Gly Ser Gly Gly Gly Ser Gly
225                 230                 235                 240
Gly Gly Gly Ser Gly Gly Gly Ser Gly Gly Gly Ser Ser Ser
                245                 250                 255
Ser Ser Lys Ala Pro Pro Ser Leu Pro Ser Pro Ser Arg Leu Pro
    260                 265                 270
Gly Pro Ser Asp Thr Pro Ile Leu Pro Gln Val Glu Cys Pro Pro Cys
                275                 280                 285
Pro Ala Pro Pro Val Ala Gly Pro Ser Val Phe Leu Phe Pro Pro Lys
    290                 295                 300
Pro Lys Asp Gln Leu Met Ile Ser Arg Thr Pro Glu Val Thr Cys Val
305                 310                 315                 320
Val Val Asp Val Ser His Glu Asp Pro Glu Val Gln Phe Asn Trp Tyr
                325                 330                 335
Val Asp Gly Val Glu Val His Asn Ala Lys Thr Lys Pro Arg Glu Glu
                340                 345                 350
Gln Phe Asn Ser Thr Phe Arg Val Val Ser Val Leu Thr Val Val His
                355                 360                 365
Gln Asp Trp Leu Asn Gly Lys Glu Tyr Lys Cys Lys Val Ser Asn Lys
    370                 375                 380
Gly Leu Pro Ala Ser Ile Glu Lys Thr Ile Ser Lys Thr Lys Gly Gln
385                 390                 395                 400
Pro Arg Glu Pro Gln Val Tyr Thr Leu Pro Pro Ser Arg Glu Glu Met
                405                 410                 415
Thr Lys Asn Gln Val Ser Leu Thr Cys Leu Val Lys Gly Phe Tyr Pro
                420                 425                 430
Ser Asp Ile Ala Val Glu Trp Glu Ser Asn Gly Gln Pro Glu Asn Asn
                435                 440                 445
Tyr Lys Thr Thr Pro Pro Met Leu Asp Ser Asp Gly Ser Phe Phe Leu
    450                 455                 460
Tyr Ser Lys Leu Thr Val Asp Lys Ser Arg Trp Gln Gln Gly Asn Val
465                 470                 475                 480
Phe Ser Cys Ser Val Leu His Glu Ala Leu His Asn His Tyr Thr Gln
                485                 490                 495
Lys Ser Leu Ser Leu Ser Pro Gly Lys
    500                 505
```

<210> SEQ ID NO 14
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of FP4I-2

<400> SEQUENCE: 14
caccctattc ccgatagctc cccccctcctg cagttcggag gccaggtgag gcagcggtac    60
ctgtacaccg acgacgctca gcagaccgaa gctcacctgg agatcaggga ggatggaacc   120
gtcggcggac tgctgaccag tccccccgag agctgctgc agctgaaggc cctgaagccc   180
ggagtcatcc agatcctggg cgtgaagacc tcccggtttc tgtgtcagcg gcccgatgga   240

```
gccctgtacg gctccctgca ttttgacccc gaggcctgta gcttcaggga gctgctgctg      300
gaagacggct acaacgtgta ccagagcgaa gctcacggac tgcccctgca cctgcctggc      360
aacaaatccc ctcacaggga ccccgctccc aggggacctg ccaggttcct gcctctgccc      420
ggactgcctc ctgctcctcc cgaacctcct ggcatcctcg ctcctcagcc ccctgatgtc      480
ggcagcagcg accctctgtc catggtcggc cccagccaag caggagccc ttcctacgct       540 tccggatccg gtggcggtgg ctccggtgga ggcggaagcg gcggtggagg atcaggcggt      600
ggaggtagcg gcggaggcgg tagctccagc tctagtaaag ctcccccctcc ttccctgccc     660 tcaccctcaa gactgcctgg accttccgac actcccatcc tgccacaggt ggagtgccct     720
ccatgtccag cacccctgt cgcaggtcca tctgtgttcc tgtttccacc caagcctaaa      780
gaccagctga tgatctcccg caccccagaa gtcacctgtg tggtcgtgga tgtgagccat      840 gaagacccg aggtccagtt caattggtac gtggatggcg tcgaggtgca aacgctaag       900 acaaaaccta gaagagagca gttcaactct acctttcgcg tcgtgagtgt gctgacagtc      960
gtgcaccagg actggctgaa tggcaaggag tataagtgca aagtgagcaa caaaggactg     1020
cctgcctcaa tcgaaaagac tatttccaag accaaggac agccaagaga gccccaggtg     1080
tacaccctgc ctccaagccg cgaagagatg actaaaaatc aggtctctct gacctgtctg     1140 gtgaagggt tttatcctag tgatatcgcc gtggaatggg agtcaaacgg tcagccagag     1200
aacaattaca agaccacacc ccctatgctg gacagcgatg ggtctttctt tctgtatagc    1260
aaactgacag tggacaagtc tcggtggcag cagggtaacg tcttctcttg cagtgtgctg     1320
cacgaagcac tgcacaatca ttacacccag aagtcactgt cactgagccc aggaaaatga    1380
```

<210> SEQ ID NO 15
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of FP4I-1

<400> SEQUENCE: 15

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Gly
            20                  25                  30

Gly Gly Ser Gly Gly Gly Gly Ser Gly Gly Gly Gly Ser His Pro Ile
        35                  40                  45

Pro Asp Ser Ser Pro Leu Leu Gln Phe Gly Gly Gln Val Arg Gln Arg
    50                  55                  60

Tyr Leu Tyr Thr Asp Asp Ala Gln Gln Thr Glu Ala His Leu Glu Ile
65                  70                  75                  80

Arg Glu Asp Gly Thr Val Gly Gly Ala Ala Asp Gln Ser Pro Glu Ser
                85                  90                  95

Leu Leu Gln Leu Lys Ala Leu Lys Pro Gly Val Ile Gln Ile Leu Gly
            100                 105                 110

Val Lys Thr Ser Arg Phe Leu Cys Gln Arg Pro Asp Gly Ala Leu Tyr
        115                 120                 125

Gly Ser Leu His Phe Asp Pro Glu Ala Cys Ser Phe Arg Glu Leu Leu
    130                 135                 140

Leu Glu Asp Gly Tyr Asn Val Tyr Gln Ser Glu Ala His Gly Leu Pro
145                 150                 155                 160

Leu His Leu Pro Gly Asn Lys Ser Pro His Arg Asp Pro Ala Pro Arg
            165                 170                 175

Gly Pro Ala Arg Phe Leu Pro Leu Pro Gly Leu Pro Pro Ala Pro Pro
            180                 185                 190

Glu Pro Pro Gly Ile Leu Ala Pro Gln Pro Pro Asp Val Gly Ser Ser
            195                 200                 205

Asp Pro Leu Ser Met Val Gly Pro Ser Gln Gly Arg Ser Pro Ser Tyr
            210                 215                 220

Ala Ser Gly Gly Gly Ser Gly Gly Gly Ser Gly Gly Gly
225                 230                 235                 240

Ser Gly Gly Gly Ser Gly Gly Gly Ser Ser Ser Ser Lys
            245                 250                 255

Ala Pro Pro Pro Ser Ser Ser Ser Lys Ala Pro Pro Pro Ser Glu
            260                 265                 270

Ser Lys Tyr Gly Pro Pro Cys Pro Pro Cys Pro Ala Pro Glu Phe Ala
            275                 280                 285

Gly Gly Pro Ser Val Phe Leu Phe Pro Pro Lys Pro Lys Asp Thr Leu
            290                 295                 300

Met Ile Ser Arg Thr Pro Glu Val Thr Cys Val Val Val Asp Val Ser
305                 310                 315                 320

Gln Glu Asp Pro Glu Val Gln Phe Asn Trp Tyr Val Asp Gly Val Glu
            325                 330                 335

Val His Asn Ala Lys Thr Lys Pro Arg Glu Glu Gln Phe Asn Ser Thr
            340                 345                 350

Tyr Arg Val Val Ser Val Leu Thr Val Leu His Gln Asp Trp Leu Asn
            355                 360                 365

Gly Lys Glu Tyr Lys Cys Lys Val Ser Asn Lys Gly Leu Pro Ser Ser
            370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Gln Glu Glu Met Thr Lys Asn Gln Val
            405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Arg Leu Thr
            450                 455                 460

Val Asp Lys Ser Arg Trp Gln Glu Gly Asn Val Phe Ser Cys Ser Val
465                 470                 475                 480

Met His Glu Ala Leu His Asn His Tyr Thr Gln Lys Ser Leu Ser Leu
            485                 490                 495

Ser Leu Gly Lys
            500

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Gly Gly Gly Ser Gly Gly Gly Ser Gly Gly
1               5                   10                  15

Gly Ser

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(2)
<223> OTHER INFORMATION: May or may not be present
<220> FEATURE:
<221> NAME/KEY: SITE
<222> LOCATION: (3)..(5)
<223> OTHER INFORMATION: May or may not be present
<220> FEATURE:
<221> NAME/KEY: SITE
<222> LOCATION: (6)..(9)
<223> OTHER INFORMATION: May or may not be present
<220> FEATURE:
<221> NAME/KEY: SITE
<222> LOCATION: (10)..(14)
<223> OTHER INFORMATION: May or may not be present
<220> FEATURE:
<223> OTHER INFORMATION: See specification as filed for detailed
      description of substitutions and preferred embodiments

<400> SEQUENCE: 17

Gly Ser Gly Gly Ser Gly Gly Gly Ser Gly Gly Gly Gly Ser
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser
1               5

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ser Gly Gly Gly Ser Gly Gly Gly Gly Ser Gly Gly Gly Gly Ser
1               5                   10                  15

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ser Gly Gly Gly Gly Ser Gly Gly Gly Gly Ser Gly Gly Gly Gly

```
                 1               5                   10                  15
Ser Gly Gly Gly Gly Ser Gly Gly Gly Ser
         20                  25

<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser
        35

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Ser Gly Gly Gly Ser Gly Gly Ser Gly Gly Gly Ser
1               5                   10                  15

Gly Gly Gly Ser
            20

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Ser Gly Gly Ser Gly Gly Ser Gly Gly Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Ser Ser Ser Lys Ala Pro Pro Pro Ser
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 25

Ser Arg Leu Pro Gly Pro Ser Asp Thr Pro Ile Leu Pro Gln
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ser Ser Ser Lys Ala Pro Pro Pro Ser Leu Pro Ser Pro Ser Arg
1               5                   10                  15

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ser Ser Ser Lys Ala Pro Pro Pro Ser Ser Ser Ser Ser Lys Ala
1               5                   10                  15

Pro Pro Pro Ser
            20

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 29

Gly Gly Gly Gly Ser
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 30

His His His His His His
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 31

His His His His His His His His
1               5

<210> SEQ ID NO 32
<211> LENGTH: 552
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Gly Gly Gly Ser Gly
        35                  40                  45

Gly Gly Gly Ser Gly Gly Gly Ser His Pro Ile Pro Asp Ser Ser
    50                  55                  60

Pro Leu Leu Gln Phe Gly Gly Gln Val Arg Gln Arg Tyr Leu Tyr Thr
65                  70                  75                  80

Asp Asp Ala Gln Gln Thr Glu Ala His Leu Glu Ile Arg Glu Asp Gly
                85                  90                  95

Thr Val Gly Gly Ala Ala Asp Gln Ser Pro Glu Ser Leu Leu Gln Leu
            100                 105                 110

Lys Ala Leu Lys Pro Gly Val Ile Gln Ile Leu Gly Val Lys Thr Ser
        115                 120                 125

Arg Phe Leu Cys Gln Arg Pro Asp Gly Ala Leu Tyr Gly Ser Leu His
    130                 135                 140

Phe Asp Pro Glu Ala Cys Ser Phe Arg Glu Leu Leu Leu Glu Asp Gly
145                 150                 155                 160

Tyr Asn Val Tyr Gln Ser Glu Ala His Gly Leu Pro Leu His Leu Pro
                165                 170                 175

Gly Asn Lys Ser Pro His Arg Asp Pro Ala Pro Arg Gly Pro Ala Arg
            180                 185                 190

Phe Leu Pro Leu Pro Gly Leu Pro Pro Ala Pro Glu Pro Pro Gly
        195                 200                 205

Ile Leu Ala Pro Gln Pro Pro Asp Val Gly Ser Ser Asp Pro Leu Ser
    210                 215                 220

Met Val Gly Pro Ser Gln Gly Arg Ser Pro Ser Tyr Ala Ser Gly Ser
225                 230                 235                 240

Gly Gly Gly Gly Ser Gly Gly Gly Ser Gly Gly Gly Ser Gly
                245                 250                 255

Gly Gly Gly Ser Gly Gly Gly Gly Ser Ser Ser Ser Ser Lys Ala Pro
```

```
                260                 265                 270
Pro Pro Ser Leu Pro Ser Pro Ser Arg Leu Pro Gly Pro Ser Asp Thr
            275                 280                 285

Pro Ile Leu Pro Gln Val Glu Cys Pro Cys Pro Ala Pro Pro Val
290                 295                 300

Ala Gly Pro Ser Val Phe Leu Phe Pro Pro Lys Pro Lys Asp Gln Leu
305                 310                 315                 320

Met Ile Ser Arg Thr Pro Glu Val Thr Cys Val Val Val Asp Val Ser
            325                 330                 335

His Glu Asp Pro Glu Val Gln Phe Asn Trp Tyr Val Asp Gly Val Glu
            340                 345                 350

Val His Asn Ala Lys Thr Lys Pro Arg Glu Glu Gln Phe Asn Ser Thr
            355                 360                 365

Phe Arg Val Val Ser Val Leu Thr Val Val His Gln Asp Trp Leu Asn
        370                 375                 380

Gly Lys Glu Tyr Lys Cys Lys Val Ser Asn Lys Gly Leu Pro Ala Ser
385                 390                 395                 400

Ile Glu Lys Thr Ile Ser Lys Thr Lys Gly Gln Pro Arg Glu Pro Gln
                405                 410                 415

Val Tyr Thr Leu Pro Pro Ser Arg Glu Glu Met Thr Lys Asn Gln Val
            420                 425                 430

Ser Leu Thr Cys Leu Val Lys Gly Phe Tyr Pro Ser Asp Ile Ala Val
            435                 440                 445

Glu Trp Glu Ser Asn Gly Gln Pro Glu Asn Asn Tyr Lys Thr Thr Pro
450                 455                 460

Pro Met Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Leu His Glu Ala Leu His Asn His Tyr Thr Gln Lys Ser Leu Ser Leu
            500                 505                 510

Ser Pro Gly Lys Val Asp Lys Ser Arg Trp Gln Gln Gly Asn Val Phe
            515                 520                 525

Ser Cys Ser Val Leu His Glu Ala Leu His Asn His Tyr Thr Gln Lys
            530                 535                 540

Ser Leu Ser Leu Ser Pro Gly Lys
545                 550

<210> SEQ ID NO 33
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Arg Ser Leu Gly Ala Leu Leu Leu Leu Ser Ala Cys Leu Ala
1               5                   10                  15

Val Ser Ala His Gly Glu Gly Thr Phe Thr Ser Asp Val Ser Ser Tyr
            20                  25                  30

Leu Glu Glu Gln Ala Ala Lys Glu Phe Ile Ala Trp Leu Val Lys Gly
        35                  40                  45

Gly Gly Gly Gly Gly Ser Gly Gly Gly Ser Gly Gly Gly Gly
    50                  55                  60
```

-continued

```
Ser His Pro Ile Pro Asp Ser Ser Pro Leu Leu Gln Phe Gly Gly Gln
 65                  70                  75                  80

Val Arg Gln Arg Tyr Leu Tyr Thr Asp Ala Gln Gln Thr Glu Ala
             85                  90                  95

His Leu Glu Ile Arg Glu Asp Gly Thr Val Gly Gly Ala Ala Asp Gln
            100                 105                 110

Ser Pro Glu Ser Leu Leu Gln Leu Lys Ala Leu Lys Pro Gly Val Ile
        115                 120                 125

Gln Ile Leu Gly Val Lys Thr Ser Arg Phe Leu Cys Gln Arg Pro Asp
    130                 135                 140

Gly Ala Leu Tyr Gly Ser Leu His Phe Asp Pro Glu Ala Cys Ser Phe
145                 150                 155                 160

Arg Glu Leu Leu Leu Glu Asp Gly Tyr Asn Val Tyr Gln Ser Glu Ala
                165                 170                 175

His Gly Leu Pro Leu His Leu Pro Gly Asn Lys Ser Pro His Arg Asp
            180                 185                 190

Pro Ala Pro Arg Gly Pro Ala Arg Phe Leu Pro Leu Pro Gly Leu Pro
        195                 200                 205

Pro Ala Pro Pro Glu Pro Pro Gly Ile Leu Ala Pro Gln Pro Pro Asp
    210                 215                 220

Val Gly Ser Ser Asp Pro Leu Ser Met Val Gly Pro Ser Gln Gly Arg
225                 230                 235                 240

Ser Pro Ser Tyr Ala Ser Gly Ser Gly Gly Gly Ser Gly Gly Gly
                245                 250                 255

Gly Ser Gly Gly Gly Ser Gly Gly Gly Ser Gly Gly Gly
            260                 265                 270

Ser Ser Ser Ser Ser Lys Ala Pro Pro Pro Ser Leu Pro Ser Pro Ser
        275                 280                 285

Arg Leu Pro Gly Pro Ser Asp Thr Pro Ile Leu Pro Gln Val Glu Cys
    290                 295                 300

Pro Pro Cys Pro Ala Pro Pro Val Ala Gly Pro Ser Val Phe Leu Phe
305                 310                 315                 320

Pro Pro Lys Pro Lys Asp Gln Leu Met Ile Ser Arg Thr Pro Glu Val
                325                 330                 335

Thr Cys Val Val Val Asp Val Ser His Glu Asp Pro Glu Val Gln Phe
            340                 345                 350

Asn Trp Tyr Val Asp Gly Val Glu Val His Asn Ala Lys Thr Lys Pro
        355                 360                 365

Arg Glu Glu Gln Phe Asn Ser Thr Phe Arg Val Val Ser Val Leu Thr
    370                 375                 380

Val Val His Gln Asp Trp Leu Asn Gly Lys Glu Tyr Lys Cys Lys Val
385                 390                 395                 400

Ser Asn Lys Gly Leu Pro Ala Ser Ile Glu Lys Thr Ile Ser Lys Thr
                405                 410                 415

Lys Gly Gln Pro Arg Glu Pro Gln Val Tyr Thr Leu Pro Pro Ser Arg
            420                 425                 430

Glu Glu Met Thr Lys Asn Gln Val Ser Leu Thr Cys Leu Val Lys Gly
        435                 440                 445

Phe Tyr Pro Ser Asp Ile Ala Val Glu Trp Glu Ser Asn Gly Gln Pro
    450                 455                 460

Glu Asn Asn Tyr Lys Thr Thr Pro Pro Met Leu Asp Ser Asp Gly Ser
465                 470                 475                 480

Phe Phe Leu Tyr Ser Lys Leu Thr Val Asp Lys Ser Arg Trp Gln Gln
```

```
            485                 490                 495
Gly Asn Val Phe Ser Cys Ser Val Leu His Glu Ala Leu His Asn His
        500                 505                 510

Tyr Thr Gln Lys Ser Leu Ser Leu Ser Pro Gly Lys
        515                 520
```

<210> SEQ ID NO 34
<211> LENGTH: 1627
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 34

```
actagtcgcc accatgagga gcctcggggc cctgctcttg ctgctgagcg cctgcctggc       60
ggtgagcgct catggcgaag gcaccttcac ctccgatgtg agcagctacc tggaagagca      120
ggccgctaaa gagtttatcg cttggctggt gaaaggagga ggaggcggag gcggaagcgg      180
cggcggaggc agcggcggag gcggcagcca ccctattccc gatagctccc cctcctgca      240
gttcggaggc caggtgaggc agcggtacct gtacaccgac gacgctcagc agaccgaagc      300
tcacctggag atcagggagg atggaaccgt cggcggagct gctgaccagt cccccgagag      360
cctgctgcag ctgaaggccc tgaagcccgg agtcatccag atcctgggcg tgaagacctc      420
ccggtttctg tgtcagcggc ccgatggagc cctgtacggc tccctgcatt ttgaccccga      480
ggcctgtagc ttcagggagc tgctgctgga agacggctac aacgtgtacc agagcgaagc      540
tcacggactg cccctgcacc tgcctggcaa caaatcccct cacagggacc ccgctcccag      600
gggacctgcc aggttcctgc ctctgcccgg actgcctcct gctcctcccg aacctcctgg      660
catcctcgct cctcagcccc ctgatgtcgg cagcagcgac cctctgtcca tggtcggccc      720
cagccaaggc aggagcccct tctacgcttc cggatccggt ggcggtggct ccggtggagg      780
cggaagcggc ggtggaggat caggcggtgg aggtagcggc ggaggcggta gctccagctc      840
tagtaaagct ccccctcctt ccctgccctc accctcaaga ctgcctggac cttccgacac      900
tcccatcctg ccacaggtgg agtgccctcc atgtccagca ccccctgtcg caggtccatc      960
tgtgttcctg tttccaccca gcctaaaga ccagctgatg atctcccgca ccccagaagt     1020
cacctgtgtg gtcgtggatg tgagccatga agaccccgag gtccagttca attggtacgt     1080
ggatggcgtc gaggtgcaca acgctaagac aaaacctaga gaagagcagt tcaactctac     1140
cttcgcgtc gtgagtgtgc tgacagtcgt gcaccaggac tggctgaatg caaggagta      1200
taagtgcaaa gtgagcaaca aaggactgcc tgcctcaatc gaaaagacta tttccaagac     1260
caaaggacag ccaagagagc cccaggtgta caccctgcct ccaagccgcg aagagatgac     1320
taaaaatcag gtctctctga cctgtctggt aaggggtttt tatcctagtg atatcgccgt     1380
ggaatgggag tcaaacggtc agccagagaa caattacaag accacacccc ctatgctgga     1440
cagcgatggg tctttctttc tgtatagcaa actgacagtg gacaagtctc ggtggcagca     1500
gggtaacgtc ttctcttgca gtgtgctgca cgaagcactg cacaatcatt acacccagaa     1560
gtcactgtca ctgagcccag gaaaatgaat ccaacgggct gatgctgcac caactgtatc     1620
cgaattc                                                              1627
```

<210> SEQ ID NO 35
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (4)..(4)
<223> OTHER INFORMATION: Glycosylation site
<220> FEATURE:
<221> NAME/KEY: SITE
<222> LOCATION: (10)..(10)
<223> OTHER INFORMATION: Glycosylation site

<400> SEQUENCE: 35

Ser Ser Ser Ser Lys Ala Pro Pro Pro Ser
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Glycosylation site
<220> FEATURE:
<221> NAME/KEY: SITE
<222> LOCATION: (7)..(7)
<223> OTHER INFORMATION: Glycosylation site

<400> SEQUENCE: 36

Ser Arg Leu Pro Gly Pro Ser Asp Thr Pro Ile Leu Pro Gln
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (4)..(4)
<223> OTHER INFORMATION: Glycosylation site
<220> FEATURE:
<221> NAME/KEY: SITE
<222> LOCATION: (10)..(10)
<223> OTHER INFORMATION: Glycosylation site
<220> FEATURE:
<221> NAME/KEY: SITE
<222> LOCATION: (15)..(15)
<223> OTHER INFORMATION: Glycosylation site

<400> SEQUENCE: 37

Ser Ser Ser Ser Lys Ala Pro Pro Pro Ser Leu Pro Ser Pro Ser Arg
1               5                   10                  15

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (4)..(4)
<223> OTHER INFORMATION: Glycosylation site
<220> FEATURE:
```

```
<221> NAME/KEY: SITE
<222> LOCATION: (10)..(10)
<223> OTHER INFORMATION: Glycosylation site
<220> FEATURE:
<221> NAME/KEY: SITE
<222> LOCATION: (15)..(15)
<223> OTHER INFORMATION: Glycosylation site
<220> FEATURE:
<221> NAME/KEY: SITE
<222> LOCATION: (21)..(21)
<223> OTHER INFORMATION: Glycosylation site

<400> SEQUENCE: 38

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25
```